United States Patent
Ranum et al.

(10) Patent No.: US 11,345,911 B2
(45) Date of Patent: May 31, 2022

(54) REGULATION OF RAN TRANSLATION BY PKR AND EIF2A-P PATHWAYS

(71) Applicant: University of Florida Research Foundation, Incorporated, Gainesville, FL (US)

(72) Inventors: Laura Ranum, Gainesville, FL (US); Tao Zu, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 273 days.

(21) Appl. No.: 16/605,992

(22) PCT Filed: Apr. 17, 2018

(86) PCT No.: PCT/US2018/028015
§ 371 (c)(1),
(2) Date: Oct. 17, 2019

(87) PCT Pub. No.: WO2018/195110
PCT Pub. Date: Oct. 25, 2018

(65) Prior Publication Data
US 2020/0140846 A1    May 7, 2020

Related U.S. Application Data

(60) Provisional application No. 62/486,424, filed on Apr. 17, 2017, provisional application No. 62/563,588, filed on Sep. 26, 2017.

(51) Int. Cl.
| | | |
|---|---|---|
| *C12N 15/10* | (2006.01) | |
| *A61K 31/7105* | (2006.01) | |
| *A61K 31/713* | (2006.01) | |
| *A61K 35/761* | (2015.01) | |
| *A61K 38/45* | (2006.01) | |
| *C07K 14/47* | (2006.01) | |
| *C12N 15/66* | (2006.01) | |

(52) U.S. Cl.
CPC .......... *C12N 15/102* (2013.01); *A61K 31/713* (2013.01); *A61K 31/7105* (2013.01); *A61K 35/761* (2013.01); *A61K 38/45* (2013.01); *C07K 14/47* (2013.01); *C12N 15/66* (2013.01); *C12N 2750/14143* (2013.01); *C12Y 207/01037* (2013.01)

(58) Field of Classification Search
CPC .. A61P 1/00; A61P 25/00; A61P 25/28; C12N 15/66; C12N 15/67; C12N 15/102; C12N 2750/14143; C12Y 2071/01037
USPC ............... 435/6.1, 91.1, 91.31, 455, 458; 514/44 A, 44 R; 530/350; 536/23.1, 24.5
See application file for complete search history.

(56) References Cited

U.S. PATENT DOCUMENTS

| | | |
|---|---|---|
| 5,011,912 A | 4/1991 | Hopp et al. |
| 6,204,008 B1 | 3/2001 | Borneman et al. |
| 6,342,581 B1 | 1/2002 | Rosen et al. |
| 7,481,997 B1 | 1/2009 | Hardy |
| 8,993,633 B2 | 3/2015 | Megeney et al. |
| 8,993,663 B2 | 3/2015 | Megeney et al. |
| 9,448,232 B2 | 9/2016 | Petrucelli et al. |
| 10,295,547 B2 | 5/2019 | Ranum et al. |
| 10,509,045 B2 | 12/2019 | Ranum et al. |
| 10,663,475 B2 | 5/2020 | Ranum et al. |
| 10,940,161 B2 | 3/2021 | Ranum et al. |
| 11,034,974 B2 | 6/2021 | Ling et al. |
| 2002/0165355 A1 | 11/2002 | Meheus et al. |
| 2003/0233675 A1 | 12/2003 | Cao et al. |
| 2007/0004729 A1 | 1/2007 | Timmer et al. |
| 2007/0014810 A1 | 1/2007 | Baker et al. |
| 2007/0036760 A1 | 2/2007 | Wilson et al. |
| 2007/0093426 A1 | 4/2007 | Wormser |
| 2008/0227699 A1 | 9/2008 | Chiba et al. |
| 2009/0074721 A1 | 3/2009 | Kim et al. |
| 2009/0143418 A1 | 6/2009 | Dixon et al. |
| 2009/0312395 A1 | 12/2009 | El-Tanani et al. |
| 2012/0076785 A1 | 3/2012 | Nikolaev et al. |
| 2012/0094299 A1 | 4/2012 | Ranum et al. |
| 2012/0220534 A1 | 8/2012 | Levin et al. |
| 2013/0115603 A9 | 5/2013 | Ranum et al. |
| 2014/0336133 A1 | 11/2014 | Miller et al. |
| 2015/0361166 A1 | 12/2015 | Edbauer et al. |
| 2016/0025747 A1 | 1/2016 | Ranum et al. |
| 2016/0096800 A1 | 4/2016 | Walter et al. |
| 2018/0292416 A1 | 10/2018 | Ranum et al. |

(Continued)

FOREIGN PATENT DOCUMENTS

| | | |
|---|---|---|
| EP | 2 837 390 A1 | 2/2015 |
| EP | 2 948 471 A1 | 12/2015 |

(Continued)

OTHER PUBLICATIONS

U.S. Appl. No. 17/322,604, filed May 17, 2021, Ranum et al.

(Continued)

*Primary Examiner* — Jane J Zara
(74) *Attorney, Agent, or Firm* — Wolf, Greenfield & Sacks, P.C.

(57) ABSTRACT

Methods and compositions for modulating repeat non-ATG protein (RAN protein) translation are provided. In some aspects, the disclosure provides methods of inhibiting RAN protein translation by contacting a cell with an effective amount of an inhibitor of eIF2 phosphorylation or an inhibitor of protein kinase R (PKR). In some embodiments, methods described by the disclosure are useful for treating diseases associated with RAN protein translation, such as certain neurodegenerative diseases.

11 Claims, 28 Drawing Sheets
Specification includes a Sequence Listing.

(56) References Cited

U.S. PATENT DOCUMENTS

| | | | |
|---|---|---|---|
| 2019/0142858 A1 | 5/2019 | Ranum et al. |
| 2019/0285652 A1 | 9/2019 | Ranum et al. |
| 2020/0140846 A1 | 5/2020 | Ranum et al. |
| 2020/0206255 A9 | 7/2020 | Ranum et al. |
| 2020/0232925 A1 | 7/2020 | Ranum et al. |
| 2020/0241013 A1 | 7/2020 | Ranum et al. |
| 2020/0268691 A1 | 8/2020 | Ranum et al. |
| 2020/0341012 A1 | 10/2020 | Ranum et al. |
| 2021/0236535 A1 | 8/2021 | Ranum et al. |
| 2021/0285970 A1 | 9/2021 | Ranum et al. |

FOREIGN PATENT DOCUMENTS

| | | |
|---|---|---|
| EP | 3440100 | 2/2019 |
| WO | WO 2001/75067 A2 | 10/2001 |
| WO | WO 2006/083800 A2 | 8/2006 |
| WO | WO 2009/144480 A1 | 12/2009 |
| WO | WO 2010/115033 A2 | 10/2010 |
| WO | WO 2010/132982 A1 | 11/2010 |
| WO | WO 2013/030588 A1 | 3/2013 |
| WO | WO 2014/114303 A1 | 7/2014 |
| WO | WO 2014/114660 A1 | 7/2014 |
| WO | WO 2014/116865 A1 | 7/2014 |
| WO | WO 2014/159247 A1 | 10/2014 |
| WO | WO 2016/025692 A1 | 2/2016 |
| WO | WO 2017/176813 A1 | 10/2017 |
| WO | WO 2018/035408 A1 | 2/2018 |

OTHER PUBLICATIONS

U.S. Appl. No. 16/695,717, filed Nov. 26, 2019, Ranum et al.
U.S. Appl. No. 17/159,288, filed Jan. 1, 2021, Ranum et al.
U.S. Appl. No. 16/650,721, filed Mar. 25, 2020, Ranum et al.
U.S. Appl. No. 16/650,016, filed Mar. 24, 2020, Ranum et al.
EP 14776090.4, Sep. 30, 2016, Extended European Search Report.
PCT/US2014/022670, Aug. 22, 2014, International Search Report and Written Opinion.
PCT/US2014/022670, Sep. 24, 2015, International Preliminary Report on Patentability.
PCT/US2016/034738, Sep. 24, 2016, International Search Report and Written Opinion.
PCT/US2016/034738, Dec. 14, 2017, International Preliminary Report on Patentability.
EP 17779695.0, Oct. 18, 2019, Supplementary Partial European Search Report.
EP 17779695.0, Jan. 7, 2020, Extended European Search Report.
PCT/US2017/026020, Jul. 7, 2017, International Search Report and Written Opinion.
PCT/US2017/062020, Oct. 18, 2018, International Preliminary Report on Patentability.
EP 18786964.9, Dec. 17, 2020, Extended European Search Report.
PCT/US2018/028015, Jul. 27, 2018, International Search Report and Written Opinion.
PCT/US2018/028015, Oct. 31, 2019, International Preliminary Report on Patentability.
PCT/US2018/052913, Jan. 15, 2019, International Search Report and Written Opinion.
PCT/US2018/052913, Apr. 9, 2020, International Preliminary Report on Patentability.
EP 18859783.5, Jun. 11, 2021, Extended European Search Report.
PCT/US2018/052745, Dec. 6, 2018, International Search Report and Written Opinion.
PCT/US2018/052745, Apr. 9, 2020, International Preliminary Report on Patentability.
Extended European Search Report, dated Sep. 30, 2016, in connection with Application No. EP 14776090.4.
International Search Report and Written Opinion, dated Aug. 22, 2014, in conenction with Application No. PCT/US2014/022670.
International Preliminary Report on Patentability, dated Sep. 24, 2015, in connection with Application No. PCT/US2014/022670.

International Search Report and Written Opinion, dated Sep. 21, 2016, in connection with Application No. PCT/US2016/034738.
International Preliminary Report on Patentability, dated Dec. 14, 2017, in connection with Application No. PCT/US2016/034738.
Supplementary Partial European Search Report, dated Oct. 18, 2019, in connection with Application No. EP 17779695.0.
Extended European Search Report, dated Jan. 7, 2020, in connection with Application No. EP 17779695.0.
International Search Report and Written Opinion, dated Jul. 7, 2017, in connection with Application No. PCT/US2017/026020.
International Preliminary Report on Patentability, dated Oct. 18, 2018, in connection with Application No. PCT/US2017/026020.
Extended European Search Report, dated Dec. 17, 2020, in connection with Application No. EP 18786964.9.
International Search Report and Written Opinion, dated Jul. 27, 2018, in connection with Application No. PCT/US2018/028015.
International Preliminary Report on Patentability, dated Oct. 31, 2019, in connection with Application No. PCT/US2018/028015.
International Search Report and Written Opinion, dated Jan. 15, 2019, in connection with Application No. PCT/US2018/052913.
International Preliminary Report on Patentability, dated Apr. 9, 2020, in connection with Application No. PCT/US2018/052913.
Extended European Search Report, dated Jun. 11, 2021, in connection with Application No. EP 18859783.5.
International Search Report and Written Opinion, dated Dec. 6, 2018, in connection with Application No. PCT/US2018/052745.
International Preliminary Report on Patentability, dated Apr. 9, 2020, in connection with Application No. PCT/US2018/052745.
[No Author Listed] EBNA1—Epstein-Barr nuclear antigen 1—Epstein-Barr virus (strain GD1) (HHV-4)—EBNA1 gene & protein, Jan. 2018. 2018. Retrieved from the internet under https://www.uniprot.org/uniprot/Q3KSS4 on Sep. 12, 2018. 6 pages.
[No Author Listed], Abstracts. Medgen. Mar. 4, 2016; 28(1):84-232. DOI: 10.1007/s11825-016-0083-5.
Ash et al., Unconventional translation of C90RF72 GGGGCC expansion generates insoluble polypeptides specific to c9FTD/ALS. Neuron. Feb. 20, 2013;77(4):639-46. doi: 10.1016/j.neuron.2013.02.004. Epub Feb. 12, 2013.
Ashizawa et al., GGCCTG repeats put a hex on Purkinje cells and motor neurons in SCA36. Neurology. Jul. 24, 2012;79(4):302-3. doi: 10.1212/WNL.0b013e31826043d9. Epub Jun. 27, 2012.
Ayhan et al., SCA8 Ran polySer protein preferentially accumulates in white matter regions and is regulated by eIF3F. Embo J. Oct. 1, 2018 ;37( 19). pii: e99023. doi: 10.15252/embj.201899023. Epub Sep. 18, 2018.
Baboonian et al., Cross reaction of antibodies to a glycine/alanine repeat sequence of Epstein-Barr virus nuclear antigen-1 with collagen, cytokeratin, and actin. Ann Rheum Dis. Nov. 1991;50(11):772-5.
Bae et al., Antibody-aided clearance of extracellular ?-synuclein prevents cell-to-cell aggregate transmission. J Neurosci. Sep. 26, 2012;32(39): 13454-69.
Bañez-Coronel et al., A pathogenic mechanism in Huntington's disease involves small CAG-repeated RNAs with neurotoxic activity. PLoS Genet. 2012;8(2):e1002481. doi: 10.1371/journal.pgen.1002481. Epub Feb. 23, 2012.
Bañez-Coronel et al., RAN Translation in Huntington Disease. Neuron. Nov. 18, 2015;88(4):667-77. doi: 10.1016/j.neuron.2015.10.038. Author manuscript.
Carroll et al., Potent and selective antisense oligonucleotides targeting single-nucleotide polymorphisms in the Huntington disease gene / allele-specific silencing of mutant huntingtin. Mol Ther. Dec. 2011;19(12):2178-85. doi: 10.1038/mt.2011.201. Epub Oct. 4, 2011.
Chen et al., Functional genomics in Drosophila models of human disease. Briefings in Functional Genomics. Aug. 22, 2012;11(5):405-415.
Cleary et al., Repeat-associated non-ATG (RAN) translation in neurological disease. Hum Mol Genet. Oct. 15, 2013;22(R1):R45-51. doi: 10.1093/hmg/ddt371. Epub Aug. 4, 2013.
Donnelly et al., RNA toxicity from the ALS/FTD C90RF72 expansion is mitigated by antisense intervention. Neuron. Oct. 16, 2013;80(2):415-28. doi: 10.1016/j.neuron.2013.10.015.

(56) References Cited

OTHER PUBLICATIONS

Duan et al., Generation of polyclonal antiserum for the detection of methylarginine proteins. J Immunol Methods. Mar. 30, 2007;320(1-2): 132-42. Epub Feb. 6, 2007.
Duellman et al., Antigen-binding properties of monoclonal antibodies reactive with EBNA1 and use in immunoaffinity chromatography. PLoS One. 2009;4(2):e4614. doi: 10.1371/journal.pone.0004614. Epub Feb. 26, 2009.
Gkogkas et al., Pharmacogenetic inhibition of eIF4E-dependent Mmp9 mRNA translation reverses fragile X syndrome-like phenotypes. Cell Rep. Dec. 11, 2014;9(5): 1742-1755. doi: 10.1016/j.celrep.2014.10.064. Epub Nov. 26, 2014.
Gómez-Tortosa et al., C9ORF72 hexanucleotide expansions of 20-22 repeats are associated with frontotemporal deterioration. Neurology. Jan. 22, 2013;80(4):366-70. doi: 10.1212/WNL.0b013e31827f08ea. Epub Jan. 2, 2013.
Hock et al., Antibodies against beta-amyloid slow cognitive decline in Alzheimer's disease. Neuron. May 22, 2003;38(4):547-54.
Jin et al., Metformin Protects Cells from Mutant Huntingtin Toxicity Through Activation of AMPK and Modulation of Mitochondrial Dynamics. Neuromolecular Med. Dec. 2016;18(4):581-592. doi: 10.1007/sl2017-016-8412-z. Epub May 25, 2016.
Kearse et al., CGG Repeat-Associated Non-AUG Translation Utilizes a Cap-Dependent Scanning Mechanism of Initiation to Produce Toxic Proteins. Mol Cell. Apr. 21, 2016;62(2):314-322. doi: 10.1016/j.molcel.2016.02.034. Epub Mar. 31, 2016.
Ma et al., Metformin therapy in a transgenic mouse model of Huntington's disease. Neurosci Lett. Jan. 10, 2007;411(2):98-103. doi: 10.1016/j.neulet.2006.10.039. Epub Nov. 15, 2006.
Mori et al., The C9orf72 GGGGCC repeat is translated into aggregating dipeptide-repeat proteins in FTLD/ALS. Science. Mar. 15, 2013;339(6125): 1335-8. doi: 10.1126/science.1232927. Epub Feb. 7, 2013. Supplementary information included.
Satoh et al., Dystrophic neurites express C9orf72 in Alzheimer's disease brains. Alzheimers Res Ther. Aug. 16, 2012;4(4):33. doi: 10.1186/alzrtl36. 13 pages.
Sha et al., Treatment implications of C9ORF72. Alzheimer's Res Ther. Nov. 27, 2012;4(6):46. doi: 10.1186/alzrt149. eCollection 2012.
Shoesmith et al., Amyotrophic lateral sclerosis: update for family physicians. Can Fam Physician. Dec. 2006;52(12): 1563-9.
Trouth et al., Myasthenia gravis: a review. Autoimmune Dis.;2012:874680. doi: 10.1155/2012/874680. Epub Oct. 31, 2012.
Wang et al., Comparative Analysis of VOCs in Exhaled Breath of Amyotrophic Lateral Sclerosis and Cervical Spondylotic Myelopathy Patients. Sci Rep. 2016;6:26120. Published May 23, 2016. doi:10.1038/srep26120.
Welnowska et al., Translation of viral mRNA without active eIF2: the case of picornaviruses. PLoS One. 2011;6(7):e22230. doi: 10.1371/journal.pone.0022230. Epub Jul. 14, 2011.
Wojciechowska et al., RAN translation and frameshifting as translational challenges at simple repeats of human neurodegenerative disorders. Nucleic Acids Res. Oct. 29, 2014;42(19): 11849-64. doi: 10.1093/nar/gku794. Epub Sep. 12, 2014.
Xiao et al., Isoform-specific antibodies reveal distinct subcellular localizations of C9orf72 in amyotrophic lateral sclerosis. Ann Neurol. Oct. 2015;78(4):568-83. doi: 10.1002/ana.24469. Epub Aug. 29, 2015.
Yanagisawa et al., Protein Binding of a DRPLA Family Through Arginine-Glutamic Acid Dipeptide repeats is Enhanced by Extended polyglutamine. Human Molecular Genetics. 2000;9(9): 1433-1442.
Yu et al., Developing therapeutic antibodies for neurodegenerative disease. Neurotherapeutics. Jul. 2013;10(3):459-72. doi: 10.1007/s13311-013-0187-4.
Zhang et al., Aggregation-prone c9FTD/ALS poly(GA) RAN-translated proteins cause neurotoxicity by inducing ER stress. Acta Neuropathol. 2014;128:505-24.
Zu et al., RAN proteins and RNA foci from antisense transcripts in C9ORF72 ALS and frontotemporal dementia. Proc Natl Acad Sci USA. Dec. 17, 2013;110(51):E4968-77. doi: 10.1073/pnas.1315438110. Epub Nov. 18, 2013.

TARBP2 inhibits PKR, reduces elF2α-P and decreases RAN

REGULATION OF RAN TRANSLATION BY PKR AND EIF2A-P PATHWAYS

RELATED APPLICATIONS

This application is a National Stage Application of PCT/US2018/028015, filed Apr. 17, 2018, entitled "REGULATION OF RAN TRANSLATION BY PRK AND EIF2A-P PATHWAYS", which claims the benefit under 35 U.S.C. § 119(e) of the filing date of U.S. Provisional Application Ser. Nos. 62/486,424, filed on Apr. 17, 2017, and 62/563,588, filed on Sep. 26, 2017, the entire contents of each of which are incorporated herein by reference.

FEDERALLY SPONSORED RESEARCH

This invention was made with government support under grant numbers NS098819, NS040389, and NS058901 awarded by the National Institutes of Health. The government has certain rights in the invention.

BACKGROUND

Since the initial discovery of repeat associated non-ATG (RAN) translation, a growing number of disease-associated repeats have been found to undergo RAN translation. Although RAN protein toxicity has been shown in transfected cells and model systems, suggesting the relevance of RAN translation to disease pathogenesis, the understanding of the mechanism of RAN translation has not improved since the initial discovery of RAN translation.

SUMMARY

Aspects of the disclosure relate to methods and compositions for reducing or inhibiting repeat-associated non-ATG (RAN) protein translation in a cell (e.g., a cell of a subject). In some aspects, the disclosure relates to the recognition that inhibiting eukaryotic initiation factor 2-alpha (eIF2α) phosphorylation (e.g., activity of eIF2α-P) and/or expression or activity of alternative eukaryotic initiation factor 2A (eIF2A) inhibits RAN protein translation. In some aspects, the disclosure relates to the recognition that inhibiting Protein Kinase R (PKR) expression or activity inhibits RAN protein translation.

Accordingly, in some aspects, the disclosure provides a method of inhibiting repeat non-ATG protein (RAN protein) translation, the method comprising contacting a cell expressing a repeat non-ATG protein (RAN protein) with an effective amount of a eukaryotic initiation factor 2 (eIF2) modulating agent. In some aspects, the disclosure provides a method of inhibiting repeat non-ATG protein (RAN protein) translation, the method comprising contacting a cell expressing a repeat non-ATG protein (RAN protein) with an effective amount of a Protein Kinase R (PKR) modulating agent.

In some aspects, the disclosure relates to the recognition that inhibition of eIF2a and/or inhibition expression or activity of eIF2A, or inhibition of PKR (e.g., inhibition of the PKR pathway), decreases RAN protein translation and accumulation in certain tissues (e.g., brain tissue) of a subject. Thus, in some aspects, the disclosure provides a method of treating a disease associated with repeat non-ATG protein (RAN protein) translation, the method comprising administering to a subject expressing a repeat non-ATG protein (RAN protein) an effective amount of a eukaryotic initiation factor 2 (eIF2) modulating agent or a PKR modulating agent (e.g., a PKR inhibitor). In some embodiments, a subject is a mammal, such as a human.

In some embodiments, a RAN protein is a poly-Alanine, poly-Leucine, poly-Serine, poly-Cysteine, poly-Glutamine, poly-Leu-Pro-Ala-Cys, poly-Gln-Ala-Gly-Arg, poly-Gly-Pro, poly-Gly-Arg, poly-Gly-Ala, or poly-Pro-Ala, poly-Pro-Arg, poly-Gly-Pro. In some embodiments, a RAN protein comprises at least 35 poly-amino acid repeats.

In some embodiments, a RAN protein is encoded by a gene associated with Huntington's disease (HD, HDL2), Fragile X Syndrome (FRAXA), Spinal Bulbar Muscular Atrophy (SBMA), Dentatorubropallidoluysian Atrophy (DRPLA), Spinocerebellar Ataxia 1 (SCA1), Spinocerebellar Ataxia 2 (SCA2), Spinocerebellar Ataxia 3 (SCA3), Spinocerebellar Ataxia 6 (SCA6), Spinocerebellar Ataxia 7 (SCA7), Spinocerebellar Ataxia 8 (SCA8), Spinocerebellar Ataxia 12 (SCA12), or Spinocerebellar Ataxia 17 (SCA17), amyotrophic lateral sclerosis (ALS), Spinocerebellar ataxia type 36 (SCA36), Spinocerebellar ataxia type 29 (SCA29), Spinocerebellar ataxia type 10 (SCA10), myotonic dystrophy type 1 (DM1), myotonic dystrophy type 2 (DM2), or Fuch's Corneal Dystrophy (e.g., CTG181).

In some embodiments, an eIF2 modulating agent inhibits phosphorylation of eIF2α, inhibits expression or activity of eIF2A, or inhibits phosphorylation of eIF2a and expression or activity of eIF2A. In some embodiments, an eIF2 modulating agent inhibits protein kinase R (PKR) expression or activity.

In some embodiments, an eIF2 modulating agent is a protein, a nucleic acid, or a small molecule.

In some embodiments, an eIF2 modulating agent is an inhibitory nucleic acid. In some embodiments, an inhibitory nucleic acid is an interfering RNA selected from the group consisting of dsRNA, siRNA, shRNA, mi-RNA, and artificial miRNA (ami-RNA). In some embodiments, an inhibitory nucleic acid is an antisense oligonucleotide (ASO) or a nucleic acid aptamer, optionally an RNA aptamer.

In some embodiments, an eIF2 modulating agent is a protein. In some embodiments, a protein is a dominant negative variant of protein kinase R (PKR). In some embodiments, dominant negative variant comprises a mutation at amino acid position 296, for example a K296R mutation.

In some embodiments, an eIF2 modulating agent or a PKR inhibitor is a small molecule. In some embodiments, a small molecule is a compound of Formula (I),

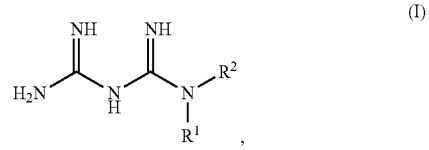

or a pharmaceutically acceptable salt, solvate, hydrate, tautomer, stereoisomer, derivative, or prodrug thereof, wherein: $R^1$ is hydrogen, optionally substituted alkyl, or a nitrogen protecting group; and $R^2$ is hydrogen, optionally substituted alkyl, or a nitrogen protecting group.

In some embodiments, R1 is hydrogen. In some embodiments, R1 is unsubstituted C1-6 alkyl.

In some embodiments, R2 is unsubstituted C1-6 alkyl. In some embodiments, R2 is unsubstituted n-butyl. In some embodiments, R2 is unsubstituted methyl. In some embodiments, R2 is substituted C1-6 alkyl. In some embodiments, R2 is of the formula:

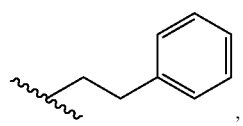 [SMILES: *CCc1ccccc1]

In some embodiments, R1 and R2 are both unsubstituted methyl.

In some embodiments, a compound of Formula (I) is of the formula:

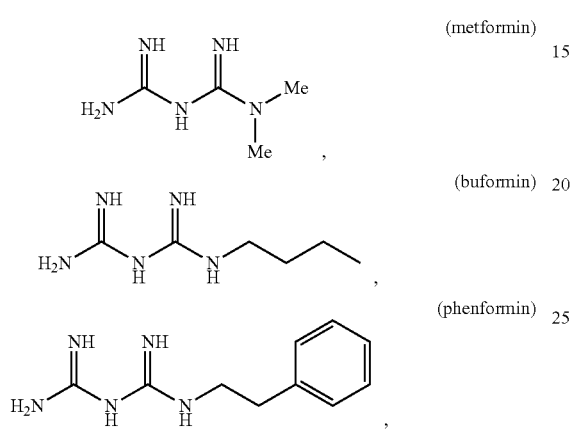

or a pharmaceutically acceptable salt, solvate, hydrate, tautomer, stereoisomer, derivative, or prodrug thereof.

In some embodiments, an eIF2 modulating agent or a PKR modulating agent (e.g., a PKR inhibitor) is delivered to the cell by a vector. In some embodiments, a vector is a viral vector, optionally a recombinant adeno-associated virus (rAAV). In some embodiments, a rAAV comprises an AAV9 capsid protein or variant thereof.

In some embodiments, a cell is located in a subject. In some embodiments, a cell is located in the brain of the subject, optionally in the white matter of the brain.

In some embodiments methods described by the disclosure further comprise administering an additional therapeutic agent for a disease associated with repeat non-ATG protein (RAN protein) translation. In some embodiments, an additional therapeutic agent is an antibody, optionally an antibody that binds specifically to a RAN repeat expansion or an antibody that binds specifically to a unique region of a RAN protein that is C-terminal to the repeat expansion, or a further inhibitory nucleic acid.

In some embodiments methods described by the disclosure, an eIF2 modulating agent or a PKR modulating agent (e.g., a PKR inhibitor) is systemically administered to the subject, optionally by injection such as intravenous injection. In some embodiments, an eIF2 modulating agent or a PKR modulating agent (e.g., a PKR inhibitor) is administered to the CNS of the subject, optionally by injection such as intracerebral ventricular (ICV) injection.

In some aspects, the disclosure provides a recombinant adeno-associated virus (rAAV) comprising: (i) a capsid protein; and (ii) a nucleic acid comprising a transgene encoding an eIF2 modulating agent operably linked to a promoter.

In some embodiments, a capsid protein is an AAV9 capsid protein, or a variant thereof. In some embodiments, a nucleic acid further comprises at least one inverted terminal repeat (ITR), optionally an AAV2 ITR. In some embodiments, a rAAV is formulated for delivery by injection. In some aspects, the disclosure provides a pharmaceutical composition comprising an rAAV as described by the disclosure and a pharmaceutically acceptable excipient.

In some aspects, the disclosure provides methods for treating and/or preventing a neurological disease associated with repeat expansions in a subject, the method comprising administering to the subject a therapeutically effective amount of a compound of Formula (I),

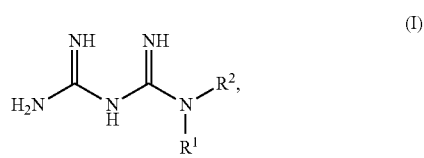

or a pharmaceutically acceptable salt, solvate, hydrate, tautomer, stereoisomer, derivative, or prodrug thereof, wherein: $R^1$ is hydrogen, optionally substituted alkyl, or a nitrogen protecting group; and $R^2$ is hydrogen, optionally substituted alkyl, or a nitrogen protecting group.

In some embodiments, R1 is hydrogen. In some embodiments, R1 is unsubstituted C1-6 alkyl.

In some embodiments, R2 is unsubstituted C1-6 alkyl. In some embodiments, R2 is unsubstituted n-butyl. In some embodiments, R2 is unsubstituted methyl. In some embodiments, R2 is substituted C1-6 alkyl. In some embodiments, R2 is of the formula:

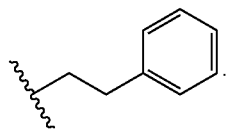 [SMILES: *CCc1ccccc1]

In some embodiments, R1 and R2 are both unsubstituted methyl.

In some embodiments, a compound of Formula (I) is of the formula:

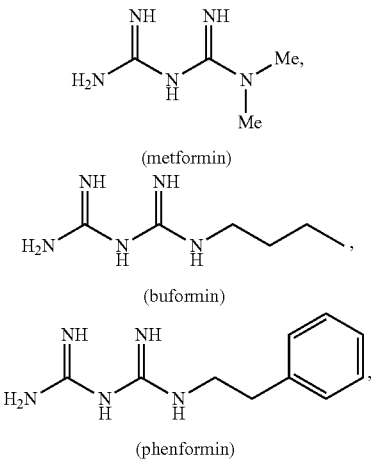

or a pharmaceutically acceptable salt, solvate, hydrate, tautomer, stereoisomer, derivative, or prodrug thereof.

In some aspects, the disclosure relates to methods of reducing the accumulation of repeat associated non-ATG protein (RAN) in a subject, tissue, or cell, the method comprising administering to the subject, or contacting the biological sample (e.g., tissue or cells) with an effective amount of metformin, or a pharmaceutically acceptable salt, solvate, hydrate, tautomer, stereoisomer, derivative, or prodrug thereof, or a pharmaceutical composition thereof. In some embodiments, a derivative of metformin is a compound of Formula (I),

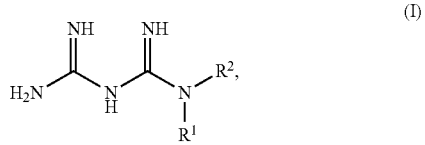

or a pharmaceutically acceptable salt, solvate, hydrate, tautomer, stereoisomer, derivative, or prodrug thereof, wherein: $R^1$ is hydrogen, optionally substituted alkyl, or a nitrogen protecting group; and $R^2$ is hydrogen, optionally substituted alkyl, or a nitrogen protecting group. In some embodiments, a derivative of metformin is buformin or phenformin.

Another aspect of the present disclosure relates to kits comprising a container with metformin, a pharmaceutically acceptable salt, solvate, hydrate, tautomer, stereoisomer, derivative, or prodrug, or a pharmaceutical composition thereof, as described herein. The kits described herein may include a single dose or multiple doses of the compound or pharmaceutical composition. The kits may be useful in a method of the disclosure. In certain embodiments, the kit further includes instructions for using the compound or pharmaceutical composition. A kit described herein may also include information (e.g. prescribing information) as required by a regulatory agency, such as the U.S. Food and Drug Administration (FDA).

These and other aspects of the application are described in more detail herein and illustrated by the following non-limiting drawings.

BRIEF DESCRIPTION OF DRAWINGS

FIG. 1A shows diagrams of CAG, CCTG and GGGCC repeat expansion constructs used to test effects of PKR on repeat associated non-ATG (RAN) translation. Constructs have 6× stop-codon cassette, two stops in each reading frame, upstream of the repeat expansions and C-terminal epitope tags. FIG. 1B shows a diagram of PKR vectors expressing wildtype (PKR-WT), the dominant negative K296R mutant form of PKR (PKR-K296R) or the C-terminal only domain (PKR-CT). FIG. 1C shows representative immunoblots of transfected HEK293T cells indicating that PKR-WT increases polyAla RAN protein from CAG expansion constructs; PKR-CT lacking the RRM motifs has no effect on polyAla RAN levels; the dominant negative mutant K296R PKR decreases polyAla RAN levels. The eIF2α-P panel shows PKR increases levels of eIF2α-P, PKR-CT has no effect and PKR K296R decreases steady state levels of eIF2α-P. FIG. 1D shows a representative immunoblot of transfected HEK293T cells indicating that PKR-WT increases polyLPAC RAN protein from CCTG expansion construct; PKR-CT has no effect on LPAC RAN levels; the dominant negative mutant K296R PKR decreases polyLPAC RAN levels. eIF2α-P panel indicates that PKR increases steady state levels of eIF2α-P; PKR-CT has no effect on steady state levels of eIF2α-P; PKR K296R decreases steady state levels of eIF2α-P. FIG. 1E shows a representative immunoblot of transfected HEK293T cells showing PKR-WT increases, PKR-CT has no effect, and mutant K296R PKR decreases polyGP RAN protein levels. eIF2α-P panel shows PKR increases, PKR-CT has no effect and PKR K296R decreases steady state levels of eIF2α-P.

FIG. 2A shows representative protein blots of HEK293T cells co-transfected with plasmids expressing WT or mutant eIF2a and a CAG expansion protein (CAGexp) show increased polyAla RAN protein levels in cells overexpressing the phosphomimetic eIF2α-S51D mutation compared to eIF2α-WT or the non-phosphorylatable eIF2α-S51A. FIG. 2B shows a representative protein blot showing polyAla, polyAla and LPAC RAN proteins expressed from CAG, CTG and CCTG repeat expansions respectively, decrease in the presence of PKR inhibitor which reduces levels of eIF2α-P. FIG. 2C shows a representative protein blot showing polyAla RAN protein levels decrease in the presence of ISIRB which inhibits downstream effects of eIF2α-P.

FIG. 3A shows schematic diagrams of AAV2/9 constructs used for AAV injections into a BAC transgenic mouse model of C9orf72 ALS/FTD containing 500 G4C2 repeats (C9-500 BAC). FIG. 3B shows representative immunohistochemical (IHC) staining of GA RAN protein aggregates in sections of the retrosplenial cortex from C9-500 BAC mice, and quantification of GA RAN protein aggregates. FIG. 3C shows openfield analysis indicating that C9-500 BAC animals treated with dominant negative PKR(K296R) show reduced center time, a phenotype indicative of anxiety-like behavior compared to EGFP control animals.

FIG. 6A shows repeat expansion constructs used for HEK293T transfections. Constructs have 6× stop-codon cassette, two stops in each reading frame, upstream of the repeat expansions and C-terminal epitope tags. FIG. 6B shows activation of PKR by hairpin-forming expanded repeat RNAs. Protein blots showing that expression of CAG, CCUG, CAGG and GGGGCC repeat expansions induce phosphorylation of PKR at sites (T446 and T451) known to be important for PKR activation. FIG. 6C shows diagrams of PKR vectors expressing wild-type (PKR-WT), the dominant negative K296R mutant form of PKR (PKR-K296R) or the inactive C-terminal domain (PKT-CT). FIG. 6D shows immunoblots of transfected HEK293T cells show PKR-WT increases polyAla RAN protein from CAG expansion constructs, PKR-CT lacking the RRM motifs has no effect on polyAla RAN levels, and the dominant negative mutant K296R PKR decreases polyAla RAN levels. FIG. 6E shows immunoblots of transfected HEK293T cells show PKR-WT increases polyLPAC RAN protein from CCTG expansion constructs, PKR-CT lacking the RRM motifs has no effect on polyLPAC RAN levels, and the dominant negative mutant K296R PKR, decreases polyLPAC RAN levels. FIG. 6F shows immunoblots of transfected HEK293T cells show PKR-WT increases polyQAGR RAN protein from CAGG expansion constructs, PKR-CT lacking the RRM motifs has no effect on polyQAGR RAN levels, and the dominant negative mutant K296R PKR, decreases polyQAGR RAN levels. FIG. 6G shows immunoblots of transfected HEK293T cells show PKR-WT increases polyGP RAN protein from GGGGCC expansion constructs, PKR-CT lacking the RRM motifs has no effect on polyGP RAN levels, and the dominant negative mutant K296R, PKR decreases polyGP RAN levels.

FIG. 7A shows immunoblots of transfected HEK293T cells. Levels of ATF-initiated polyGln protein are not affected by overexpression of PKR-WT, PKR-CT or PKR K296R. FIG. 7B shows immunoblots of transfected HEK293T cells indicating overexpression of PKR-WT increases polyLPAC RAN protein from CCTG expansion constructs, PKR-CT has no effect, and the dominant negative mutant PKR K296R decreases polyLPAC RAN levels in all three reading frames.

FIG. 8A shows protein blots of HEK293T cells co-transfected with plasmids expressing WT or mutant eIF2α and a CAGexp show increased polyAla RAN protein levels in cells overexpressing the phosphomimetic eIF2α-S51D mutation compared to eIF2α-WT or the non-phosphorylatable eIF2α-S51A. FIG. 8B shows protein blot showing the PKR inhibitor, transactivation response element RNA-binding protein (TARBP2), reduces levels of RAN polyAla expressed from CAG and CUG expansion RNAs and RAN polyLPAC expressed from CCUG repeats. Additionally, TARBP2 reduces levels of p-eIF2α. FIG. 8C shows a protein blot showing polyAla RAN protein levels, which are elevated with PKR-WT overexpression are decrease when also treated with the integrated stress response inhibitor (ISRIB) which inhibits downstream effects of p-eIF2α.

FIG. 10A shows schematic diagrams of EGFP control and PKR-K296R AAV2/9 constructs used for intracerebral ventricular (ICV) injections into BAC transgenic C9orf72 ALS/FTD mice containing 500 G4C2 repeats (C9-500 BAC). ICV injections were performed at P0 injections with AAV2/9 virus expressing either EGFP or the dominant negative form of PKR(K296R) and animals were sacrificed for analysis at 3 months of age. FIG. 10B shows mesoscale detection assays (MSD) of brain lysates shows PKR-K296R treated mice have lower levels of soluble GP RAN proteins. FIG. 10C shows representative immunohistochemistry (IHC) staining (brown color) of GA RAN protein aggregates in sections of the retrosplenial cortex from C9-500 BAC mice with quantification showing GA RAN protein aggregates are reduced in PKR-K296R treated mice compared to controls. Analysis was done in a blinded fashion. FIG. 10D shows open-field analyses showing C9-500 BAC mice treated with PKR-K296R show reduced center time, a phenotype indicative of anxiety-like behavior compared to EGFP control animals.

FIG. 11A shows a protein blot indicating that metformin reduces RAN protein expression in HEK293T cells transiently transfected with CAG, CCTG, CAGG and G4C2 expansion constructs. FIG. 11B shows data indicating that metformin reduces levels of p-PKR (T446 and T451) in cells transfected with repeat expansion constructs. FIG. 11C is a schematic diagram showing study design for two metformin treatment groups, with treatment at 5 mM metformin from 2 to 5 months of age or from six to 9 months of age. FIG. 11D shows data quantifying GA aggregates and indicates a reduction in GA aggregates in mice treated with 5 mM metformin in their drinking water from 2-5 months compared to untreated C9-500 mice. FIG. 11E shows quantification of GFAP staining, indicating decreased levels of reactive gliosis in C9-500 metformin treated mice compared to C9-500 control animals. FIG. 11F shows DigiGait analyses indicating that of eight parameters that differed between untreated C9-500 and NT controls, 6 of these parameters improved in C9-500 animals treated with metformin. Example data from of four of these eight parameters are shown. FIG. 11G shows open-field analyses showing decreased center time in C9-500 animals is normalized in C9-500 animals treated with metformin. FIG. 11H shows data from MSD assays indicating soluble GP levels are reduced in C9-500 animals treated with metformin compared to C9-500 controls. FIG. 11I shows GA aggregates are reduced in C9-500 animals treated with metformin compared to C9-500 controls. FIG. 11J is a schematic showing chronic activation of the PKR pathway by repeat expansion RNAs favors RAN translation through the integrated stress response and eIF2α phosphorylation.

In FIG. 13B, the lane labeled KMQ has a methionine encoding ATG immediately 5' to the CAG repeat expansion and located within the polyGln reading frame. The KKQ vector contains a CAG expansion without an AUG initiation codon, and indicates: Ser-Flag, Ala-HA, Gln-Myc. These constructs contain epitope tags that are incorporated into the C-terminal regions of the ATG-initiated poly-Gln and non-ATG initiated RAN proteins (poly-Gln, poly-Leu-Pro-Ala-Cys and poly-Gly-Pro) which are expressed across these repeat expansions. The lane labeled CCTG expresses the following RAN proteins: LPAC-Flag, LPAC-HA, LPAC-Myc. The lane labeled G4C2 is designed to detect the following RAN proteins: GP-Flag, GR-HA, GA-Myc. Treatment of the transfected HEK293T cells with metformin shows reduced RAN protein levels of the following RAN proteins of poly-LPAC (poly-Leucine-Proline-Alanine-Cysteine in all three reading frames, poly-Ala, and poly-GP (poly-glycine-proline).

DETAILED DESCRIPTION

Figure 1A:
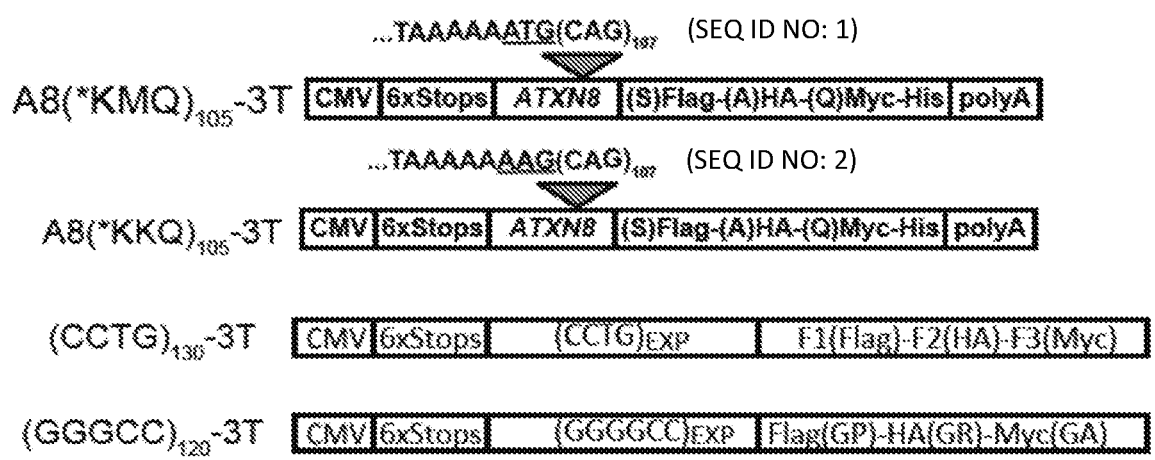
FIGS. 1A-1E show protein kinase R (PKR) regulates RAN translation of CAG, CCTG, G4C2 expansions through eIF2α-P pathway.

In eukaryotes, the protein translation machinery including ribosomes, initiation factors (eIFs) and specific steps of translation initiation and elongation are well conserved. Eukaryotic initiation factor 2 (eIF2) is a multiprotein complex that is involved with the initiation phase of eukaryotic protein translation. Generally, in humans eIF2 comprises three non-identical subunits (e.g., eIF2α, eIF2β, and eIF2γ). Typically, eIF2α is involved in initiation of translation, forming a ternary complex with guanosine-triphosphate (GTP) and the initiator methionyl initiator transfer RNA.

RAN Protein Translation

Aspects of the application relate to methods and compositions for reducing the expression of repeat-associated non-ATG (RAN) proteins. A "RAN protein (repeat-associated non-ATG translated protein)" is a polypeptide translated from bidirectionally transcribed sense or antisense RNA sequences carrying a nucleotide expansion in the absence of an AUG initiation codon. Generally, RAN proteins comprise expansion repeats of a single amino acid, di-amino acid, tri-amino acid, or quad-amino acid (e.g., tetra-amino acid), termed poly amino acid repeats. For example, "AAAAAAAAAAAAAAAAAAAA" (poly-Alanine) (SEQ ID NO: 3), "LLLLLLLLLLLLLLLLLLLL" (poly-Leucine) (SEQ ID NO: 4), "SSSSSSSSSSSSSSSSSSSS" (poly-Serine) (SEQ ID NO: 5), or "CCCCCCCCCCCCCCCCCCCC" (poly-Cysteine) (SEQ ID NO: 6) are poly amino acid repeats that are each 20 amino acid residues in length. Examples of di-amino acid RAN proteins include GPGPGPGPGPGPGPGPGPGP (poly-GP) (SEQ ID NO: 7), GAGAGAGAGAGAGAGAGAGA (poly-GA) (SEQ ID NO: 8), GRGRGRGRGRGRGRGRGRGR (poly-GR) (SEQ ID NO: 9), PAPAPAPAPAPAPAPAPAPA (poly-PA) (SEQ ID NO: 10), and PRPRPRPRPRPRPRPRPRPR (poly-PR) (SEQ ID NO: 11). Examples of tetra-amino acid repeats include LPACLPACLPAC (e.g., poly-LPAC) (SEQ ID NO: 12) and QAGRQAGRQAGR (e.g., poly-QAGR) (SEQ ID NO: 13). RAN proteins can have a poly amino acid repeat of at least 25, at least 30, at least 40, at least 50, at least 60, at least 70, at least 80, at least 90, at least 100, or at least 200 amino acid residues in length. In some embodiments, a RAN protein has a poly amino acid repeat more than 200 amino acid residues in length.

Generally, RAN proteins are translated from abnormal repeat expansions (e.g., CAG repeats) of DNA. Without wishing to be bound by any particular theory, RAN protein accumulation (e.g., in the nucleus or cytoplasm of a cell) disrupts cellular function and induces cellular toxicity. In some embodiments, translation and accumulation of RAN proteins is associated with a disease or disorder, for example a neurodegenerative disease or disorder. Examples of disorders and diseases associated with RAN protein translation and accumulation include but are not limited to spinocerebellar ataxia type 8 (SCA8), myotonic dystrophy type 1 (DM1), fragile X tremor ataxia syndrome (FXTAS), and C9ORF72 amyotrophic lateral sclerosis/frontotemporal dementia (ALS/FTD). Accordingly, methods and compositions described in this application are useful, in some embodiments, for treating one or more RAN protein associated diseases or conditions in a subject in need thereof. In some embodiments, a subject is a mammalian subject. In some embodiments, a subject is a human subject.

Inhibition of eIF2α-P, eIF2A, and PKR

Aspects of the disclosure relate to the recognition that inhibition of eIF2α phosphorylation (e.g., eIF2α-P) reduces RAN protein translation and accumulation in cells. In some aspects, the disclosure is based on the recognition that an alternative mammalian eIF (e.g., eIF2A) can serve as an alternative eukaryotic initiation factor for RAN across a variety of disease causing expansion mutations. In some aspects, the disclosure is based on the recognition that inhibition of Protein Kinase R (PKR) reduces RAN protein translation and accumulation in cells.

Accordingly, in some aspects, the disclosure provides methods for inhibiting repeat non-ATG protein (RAN protein) translation, the method comprising contacting a cell expressing a repeat non-ATG protein (RAN protein) with an effective amount of a eukaryotic initiation factor 2 (eIF2) modulating agent or a PKR modulating agent.

As used herein, a "modulator of eIF2" refers to an agent that directly or indirectly affects the expression level or activity of an eIF2 protein complex, or an eIF2 complex subunit (e.g., eIF2α, eIF2β, eIF2γ, etc.). A modulator can be an activator of eIF2 or an eIF2 subunit (e.g., increase the expression or activity of eIF2 or an eIF2 subunit) or an inhibitor of eIF2 or an eIF2 subunit (e.g., decrease the expression or activity of eIF2 or an eIF2 subunit). In some embodiments, an eIF2 modulator increases or decreases expression and/or activity of eIF2 or an eIF2 subunit in a cell or subject relative to a cell or subject that has not been administered an eIF2 modulator. In some embodiments, an eIF2 inhibitor is a protein, nucleic acid, or small molecule.

Generally, a direct modulator functions by interacting with (e.g., interacting with or binding to) a gene encoding eIF2 (or an eIF2 subunit), or an eIF2 protein complex, or an eIF2 subunit. Generally, an indirect modulator functions by interacting with a gene or protein that regulates the expression or activity of eIF2 or an eIF2 subunit (e.g., does not directly interact with a gene or protein encoding eIF2 or an eIF2 subunit).

In some aspects the disclosure relates to the recognition that inhibiting phosphorylation of eIF2α (e.g., phosphorylation of eIF2α at Ser 51) reduces RAN protein translation (e.g., RAN protein translation in a cell). Without wishing to be bound by any particular theory, inhibitors of certain serine kinases that phosphorylate eIF2α (e.g., protein kinase R (PKR), etc.) are useful, in some embodiments for inhibiting RAN protein translation and/or RAN protein aggregation in a cell (e.g., cells of a subject). Thus, in some embodiments, a modulator of eIF2 is an inhibitor of a serine/threonine kinase. Examples of serine/threonine kinases include but are not limited to protein kinase A (PKA), protein kinase C (PKC), Mos/Raf kinases, mitogen-activated protein kinases (MAPKs), protein kinase B (AKT kinase), etc. In some embodiments, an eIF2 modulating agent is a protein kinase R (PKR) inhibitor.

As used herein, a "modulator of PKR" refers to an agent that directly or indirectly affects the expression level or activity of Protein Kinase R (PKR). A modulator can be an activator of PKR (e.g., increase the expression or activity of PKR) or an inhibitor of PKR (e.g., decrease the expression or activity of PKR). In some embodiments, an PKR modulator increases or decreases expression and/or activity of PKR in a cell or subject relative to a cell or subject that has not been administered a PKR modulator. In some embodiments, a PKR inhibitor is a protein, nucleic acid, or small molecule.

Generally, a direct modulator functions by interacting with (e.g., interacting with or binding to) a gene encoding PKR. Generally, an indirect modulator functions by interacting with a gene or protein that regulates the expression or activity of PKR (e.g., does not directly interact with a gene or protein encoding PKR).

The disclosure relates, in part, to the certain variants of protein kinase R (PKR) that function in a dominant negative manner to inhibit phosphorylation of eIF2α and are therefore useful for reducing RAN protein translation in a cell. As used herein, "protein kinase R (PKR) variant" refers to a protein comprising an amino acid sequence that is at least 70%, at least 80%, at least 90%, at least 95%, at least 96%, at least 97%, at least 98%, or at least 99% identical to a wild-type protein kinase R (PKR) (e.g., GenBank Accession No. NP_002750.1), wherein the variant protein comprises at least one amino acid variation (also referred to sometimes as "mutation") relative to the amino acid sequence of the wild-type PKR.

In some embodiments, the amino acid sequence of a PKR variant is at least 75%, at least 85%, at least 95%, at least 96%, at least 97%, at least 98%, at least 99%, at least 99.5%, at least 99.6%, at least 99.7%, at least 99.8%, or at least 99.9% identical to the amino acid sequence of wild-type PKR. In some embodiments, the amino acid sequence is about 95-99.9% identical to the amino acid sequence of wild-type PKR. In some embodiments, the protein comprises at least 1, at least 2, at least 3, at least 4, at least 5, at least 6, at least 7, at least 8, at least 9, at least 10, at least 11, at least 12, at least 13, at least 14, or at least 15 different amino acid sequence variations as compared to the sequence of amino acids set forth in the amino acid sequence of wild-type PKR. In some embodiments, a PKR variant comprises a mutation at position 296 (e.g., position 296 of a human wild-type PKR). In some embodiments, the mutation at position 296 is K296R.

The disclosure relates, in part, to the recognition that under certain conditions, eIF2A functions as an alternative translation initiation factor for RAN translation. Thus, in some embodiments, a modulator of eIF2 is an inhibitor of eIF2A.

In some embodiments, a modulator of eIF2 or PKR is a selective modulator. A "selective modulator" refers to a modulator of eIF2 or PKR that preferentially modulates activity or expression of one type of eIF2 subunit compared with other types of eIF2 subunits, or modulates activity or expression of PKR preferentially compared to other kinases. In some embodiments, a modulator of eIF2 is a selective modulator of eIF2α. In some embodiments, a modulator of eIF2 is a selective modulator of eIF2A. In some embodiments, a modulator of eIF2 is a selective modulator of protein kinase R (PKR), such as a selective PKR inhibitor.

Examples of proteins that inhibit eiF2 (e.g., an eIF2 subunit) include but are not limited to polyclonal anti-eIF2 antibodies, monoclonal anti-eIF2 antibodies, etc. Examples of nucleic acid molecules that inhibit eiF2 (e.g., an eIF2 subunit) include but are not limited to dsRNA, siRNA, miRNA, etc. that target a gene encoding an eIF2 subunit (e.g., a gene encoding the mRNA set forth in GenBank Accession No. NM_004094.4). Examples of small molecule inhibitors of eIF2 include but are not limited to LY 364947, eIF-2α Inhibitor II Sal003, etc.

Examples of proteins that inhibit PKR include but are not limited to certain dominant negative PKR variants (e.g., K296R PKR mutant), TARBP2, etc. Examples of nucleic acid molecules that inhibit PKR include but are not limited to dsRNA, siRNA, miRNA, etc. that target a gene encoding a PKR. Examples of small molecule inhibitors of PKR include but are not limited to 6-amino-3-methyl-2-oxo-N-phenyl-2,3-dihydro-1H-benzo[d]imidazole-1-carboxamide, N-[2-(1H-indol-3-yl)ethyl]-4-(2-methyl-1H-indol-3-yl)pyrimidin-2-amine, metformin, buformin, phenformin, etc.

Examples of nucleic acid molecules that inhibit eIF2A include but are not limited to dsRNA, siRNA, miRNA, etc. that target a gene encoding a eIF2A (e.g., a gene encoding the mRNA set forth in GenBank Accession No. NM_032025.4). Examples of small molecule inhibitors of eIF2A include but are not limited to salubrinal, Sal003, ISRIB, etc.

In some embodiments, the eIF2 modulating agent or PKR modulating agent is an inhibitory nucleic acid. In some embodiments, the inhibitory nucleic acid is an interfering RNA selected from the group consisting of dsRNA, siRNA, shRNA, mi-RNA, and ami-RNA. In some embodiments, the inhibitory nucleic acid is an antisense nucleic acid (e.g., an antisense oligonucleotide (ASO)) or a nucleic acid aptamer (e.g., an RNA aptamer). Generally, an inhibitory RNA molecule can be unmodified or modified. In some embodiments, an inhibitory RNA molecule comprises one or more modified oligonucleotides, e.g., phosphorothioate-, 2'-O-methyl-, etc.-modified oligonucleotides, as such modifications have been recognized in the art as improving the stability of oligonucleotides in vivo.

In some embodiments, the interfering RNA comprises a sequence that is complementary with between 5 and 50 continuous nucleotides (e.g., 5, 6, 7, 8, 9, 10, 11, 12, 13, 14, 15, 16, 17, 18, 19, 20, 21, 22, 23, 24, 25, about 30, about 35, about 40, or about 50 continuous nucleotides) of a nucleic acid sequence (such as an RNA sequence) encoding an eIF2 subunit or a nucleic acid sequence (such as an RNA sequence) encoding PKR.

In some embodiments, the eIF2 modulating agent or PKR modulating agent is a small molecule (e.g., a compound) Formula (I),

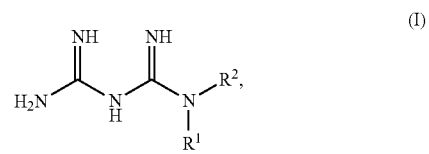

or a pharmaceutically acceptable salt, solvate, hydrate, tautomer, stereoisomer, derivative, or prodrug thereof, wherein: $R^1$ is hydrogen, optionally substituted alkyl, or a nitrogen protecting group; and $R^2$ is hydrogen, optionally substituted alkyl, or a nitrogen protecting group.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. Metformin may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\, H_2O$, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates ($R \cdot 0.5\, H_2O$)), and polyhydrates (x is a number greater than 1, e.g., dihydrates ($R \cdot 2\, H_2O$) and hexahydrates ($R \cdot 6\, H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

In certain embodiments, R1 is hydrogen. The term "optionally substituted" refers to a group that is substituted or unsubstituted. Exemplary carbon atom substituents include, but are not limited to, halogen, —CN, —NO2, —N3, —SO2H, —SO3H, —OH, —NH2, C3-10 carbocyclyl, 3-14 membered heterocyclyl, C6-14 aryl, and 5-14 membered heteroaryl. "Carbocyclyl" refers to a radical of a non-aromatic cyclic hydrocarbon group having from 3 to 10 ring carbon atoms ("C3-10 carbocyclyl") and zero heteroatoms in the non-aromatic ring system. The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_6$-14 aryl"). The term "heteroaryl" refers to a radical of a 5-14 membered monocyclic or polycyclic (e.g., bicyclic, tricyclic) 4n+2 aromatic ring system (e.g., having 6, 10, or 14 it electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl").

In certain embodiments, R1 is optionally substituted alkyl. In certain embodiments, R1 is unsubstituted C1-6 alkyl. In certain embodiments, R1 is unsubstituted methyl, unsubstituted ethyl, unsubstituted propyl, or unsubstituted butyl. In certain embodiments, R1 is unsubstituted methyl. In certain embodiments, R1 is unsubstituted n-butyl. In certain embodiments, R1 is a nitrogen protecting group (e.g., amide groups, carbamate groups, or sulfonamide groups (e.g., t-butyl carbamate (BOC), benzyl, benzyl carbamate (Cbz), or benzyloxymethyl)). In certain embodiments, R2 is hydrogen. In certain embodiments, R2 is optionally substituted alkyl. In certain embodiments, R2 is optionally substituted C1-6 alkyl. In certain embodiments, R1 is unsubstituted methyl, unsubstituted ethyl, unsubstituted propyl, or unsubstituted butyl. In certain embodiments, R1 is unsubstituted methyl. In certain embodiments, R2 is substituted C1-6 alkyl. In certain embodiments, R2 is optionally substituted methyl. In certain embodiments, R2 is optionally substituted ethyl. In certain embodiments, R2 is substituted ethyl. In certain embodiments, R2 is of the formula:

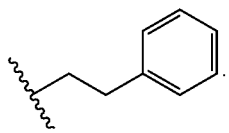 [SMILES: *CCc1ccccc1]

In certain embodiments, R2 is substituted propyl. In certain embodiments, R2 is substituted butyl. In certain embodiments, R1 and R2 are both unsubstituted methyl. In certain embodiments, R2 is a nitrogen protecting group (e.g., amide groups, carbamate groups, or sulfonamide groups (e.g., t-butyl carbamate (BOC), benzyl, benzyl carbamate (Cbz), or benzyloxymethyl)).

In some embodiments, a compound of Formula (I) is of the formula:

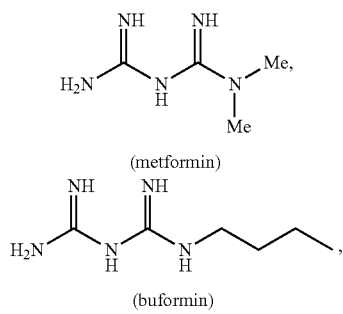

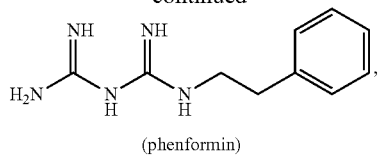

(phenformin)

or a pharmaceutically acceptable salt, solvate, hydrate, tautomer, stereoisomer, derivative, or prodrug thereof.

In some embodiments, one or more modulators (e.g., one or more activators, or one or more inhibitors) of one or more subunits of eIF2 and/or PKR are administered to a subject to treat a disease associated with an expansion of a nucleic acid repeat (e.g., associated with a repeat-associated non-ATG translation). For example, in some embodiments, a subject is administered 2, 3, 4, 5, 6, 7, 8, 9, or 10 modulators (e.g., proteins, nucleic acids, small molecules, etc.) of one or more subunits of eIF2 and/or 2, 3, 4, 5, 6, 7, 8, 9, or 10 modulators of PKR (e.g., proteins, nucleic acids, small molecules, etc.). In some embodiments a subject is administered an inhibitor of eIF2α and an inhibitor of eIF2A.

Pharmaceutical Compositions

The present disclosure also provides pharmaceutical compositions comprising a compound of Formula (I) (e.g., metformin, buformin, phenformin, etc.) and optionally a pharmaceutically acceptable excipient. In certain embodiments, the pharmaceutical composition comprises a compound of Formula (I) (e.g., metformin, buformin, phenformin, etc.), or a pharmaceutically acceptable salt thereof, and a pharmaceutically acceptable excipient.

In certain embodiments, a compound of Formula (I) (e.g., metformin, buformin, phenformin, etc.) is provided in an effective amount in the pharmaceutical composition. In certain embodiments, the effective amount is a therapeutically effective amount. In certain embodiments, the effective amount is a prophylactically effective amount. In certain embodiments, a therapeutically effective amount is an amount effective in reducing repeat expansions. In certain embodiments, a therapeutically effective amount is an amount effective in reducing the transcription of RNAs that produce RAN proteins. In certain embodiments, a therapeutically effective amount is an amount effective in reducing the translation of RAN proteins. In certain embodiments, a therapeutically effective amount is an amount effective in reducing the level of one or more RAN proteins in a subject. In certain embodiments, a therapeutically effective amount is an amount effective for treating a neurological disease associated with repeat expansions. In certain embodiments, a therapeutically effective amount is an amount effective in reducing the level of one or more RAN proteins and treating a neurological disease associated with repeat expansions. In certain embodiments, a therapeutically effective amount is an amount effective in reducing the accumulation of RAN proteins.

In certain embodiments, the effective amount is an amount effective in reducing the level of RAN proteins by at least 10%, at least 20%, at least 30%, at least 40%, at least 50%, at least 60%, at least 70%, at least 80%, at least 90%, at least 95%, or at least 98% (e.g., the level of RAN proteins relative to the level of RAN proteins in a cell or subject that has not been administered an eIF2 modulator or PKR modulator). In certain embodiments, the effective amount is an amount effective in reducing the translation of RAN proteins by at least 10%, at least 20%, at least 30%, at least 40%, at least 50%, at least 60%, at least 70%, at least 80%, at least 90%, at least 95%, or at least 98% (e.g., the level of RAN proteins relative the level of RAN proteins in a cell or subject that has not been administered an eIF2 modulator or PKR modulator).

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof. The exemplary liquid dosage forms in certain embodiments are formulated for ease of swallowing, or for administration via feeding tube.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

A compound of Formula (I) (e.g., metformin, buformin, phenformin, etc.) provided herein is typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

A compound of Formula (I) (e.g., metformin, buformin, phenformin, etc.) and compositions thereof provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound of Formula (I) (e.g., metformin, buformin, phenformin, etc.) required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the biological sample, tissue, or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the biological sample, tissue, or cell is one dose per day. In certain embodiments, the frequency of administering the multiple doses to the subject or applying the multiple doses to the biological sample, tissue, or cell is two doses per day. In certain embodiments, the frequency of administering the multiple doses to the subject or applying the multiple doses to the biological sample, tissue, or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, eight months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

In one aspect, the method comprises administering to the subject a therapeutically effective amount of metformin:

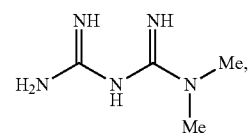

or a pharmaceutically acceptable salt, solvate, hydrate, tautomer, stereoisomer, derivative, or prodrug thereof. In certain embodiments, metformin is formulated as a metformin hydrochloride tablet. In certain embodiments, metformin is formulated as a metformin hydrochloride extended release tablet. In certain embodiments, metformin is formulated as a metformin succinate or metformin fumurate salt. Metformin and compositions thereof, in certain embodiments, is administered via an enteral (e.g., oral) route.

In certain embodiments, a compound of Formula (I) (e.g., metformin, buformin, phenformin, etc.) is administered in doses of 500 mg metformin twice a day or doses of 850 mg metformin once a day. In certain embodiments, a compound of Formula (I) (e.g., metformin, buformin, phenformin, etc.) is administered in doses of at least 825 mg metformin three times a day. In certain embodiments, a compound of Formula (I) (e.g., metformin, buformin, phenformin, etc.) is administered in doses of 825 mg metformin three times a day. In certain embodiments, a compound of Formula (I) (e.g., metformin, buformin, phenformin, etc.) is administered in doses of 500 mg metformin once a day. In certain embodiments, a compound of Formula (I) (e.g., metformin, buformin, phenformin, etc.) is administered in doses of 1000 mg metformin once a day. Doses of a compound of Formula (I) (e.g., metformin, buformin, phenformin, etc.), in certain embodiments, are given with meals. In certain embodiments, the method comprises administering to the subject a compound of Formula (I) (e.g., metformin, buformin, phenformin, etc.) over a period between 10 days to 30 days. In certain embodiments, the duration between the first dose and last dose of the multiple doses of a compound of Formula (I) (e.g., metformin, buformin, phenformin, etc.) is 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days. In certain embodiments, the duration between the first dose and last dose of the multiple doses of a compound of Formula (I) (e.g., metformin, buformin, phenformin, etc.) is at least the following number of days: 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days. In certain embodiments, the duration between the first dose and last dose of the multiple doses of a compound of Formula (I) (e.g., metformin, buformin, phenformin, etc.) is 1 month, 2 months, 3 months, 4 months, 5 months, 6 months, multiple months, at least one year, multiple years, at least one decade, or multiple decades. In certain embodiments, the doses of a compound of Formula (I) (e.g., metformin, buformin, phenformin, etc.) are administered indefinitely. In certain embodiments, the doses of a compound of Formula (I) (e.g., metformin, buformin, phenformin, etc.) are administered over a lifetime of the subject. In certain embodiments, a dose described herein is at least 500 mg, 600 mg, 650 mg, 750 mg, 700 mg, 800 mg, 825 mg, 850 mg, 900 mg, 950 mg, 1000 mg, 1500 mg, 2000 mg, 2500 mg, 3000 mg, 3500 mg, 4000 mg, 5000 mg, 8000 mg, 9000 mg, or 10,000 mg of a compound of Formula (I) (e.g., metformin, buformin, phenformin, etc.). In certain embodiments, the duration between the first dose and last dose of the multiple doses of a compound of Formula (I) (e.g., metformin, buformin, phenformin, etc.) is based on the duration required to prevent the accumulation of RAN proteins in a subject. In certain embodiments, the duration between the first dose and last dose of the multiple doses of a compound of Formula (I) (e.g., metformin, buformin, phenformin, etc.) is based on the duration required to reduce the level of RAN proteins in a subject. In certain embodiments, the multiple doses of a compound of Formula (I) (e.g., metformin, buformin, phenformin, etc.) are administered as prophylactic treatment to reduce the level of RAN proteins in a subject. The prophylactic treatment is long-term, in certain embodiments. In certain embodiments, the multiple doses of a compound of Formula (I) (e.g., metformin, buformin, phenformin, etc.) are administered as long-term therapeutic treatment to reduce the level of RAN proteins in a subject.

The subject, in certain embodiments, has a microsatellite expansion mutation including but not limited to mutations that cause: C9orf72 ALS or C9orf72 FTD, myotonic dystrophy type 1 (DM1) and myotonic dystrophy type 2 (DM2); spinocerebellar ataxia types 1, 2, 3, 6, 7, 8, 10, 12, 17, 31, and 36; spinal bulbar muscular atrophy; dentatorubral-pallidoluysian atrophy (DRPLA); Huntington's disease (HD); Fragile X Tremor Ataxia Syndrome (FXTAS); Huntington's disease-like 2 syndrome (HDL2); Fragile X syndrome (FXS); disorders related to 7p11.2 folate-sensitive fragile site FRA7A; disorders related to folate-sensitive fragile site 2q11 FRA2A; and Fragile XE syndrome (FRAXE).

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound of Formula (I) (e.g., metformin, buformin, phenformin, etc.) or compositions thereof, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in inhibiting the activity of a protein kinase (e.g., CDK) in a subject, biological sample, tissue, or cell), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

A compound of Formula (I) (e.g., metformin, buformin, phenformin, etc.) or compositions thereof can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., neurological disease). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In some embodiments, additional pharmaceutical agents include, but are not limited to, cardiovascular agents, anti-diabetic agents, and agents for treating and/or preventing a neurological disease. The additional pharmaceutical agents include, but are not limited to, anti-inflammatory agents or compounds (e.g., turmeric). In some embodiments, the additional pharmaceutical agent is an ant-RAN antibody, for example anti-polyGA, anti-polyGP, anti-polyPA, anti-polyPR, anti-polyGR, anti-polyAla, anti-polySer, anti-polyLeu, anti-polyLPAC, anti-polyQAGR, etc.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound of Formula (I) (e.g., metformin, buformin, phenformin, etc.) or compositions thereof described herein. In certain embodiments, the kits are useful for treating a neurological disease) in a subject in need thereof. In certain embodiments, the kits are useful for preventing a neurological disease) in a subject in need thereof. In certain embodiments, the kits are useful for reducing the level of one or more RAN proteins (e.g., reducing the expression of RAN proteins) in a subject, biological sample, tissue, or cell. In certain embodiments, the kits are useful for reducing the accumulation of RAN proteins in a subject, biological sample, tissue, or cell. In certain embodiments, the kits are useful for modulating (e.g., reducing or inhibiting) RAN protein translation in a subject, biological sample, tissue, or cell.

In certain embodiments, a kit described herein further includes instructions for using metformin, or pharmaceutical composition thereof, included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., a neurological disease) in a subject in need thereof. In certain embodiments, the kits and instructions provide for preventing a disease (e.g., a neurological disease) in a subject in need thereof. In certain embodiments, the kits and instructions provide for reducing the level of one or more RAN proteins in a subject, biological sample, tissue, or cell. In certain embodiments, the kits and instructions provide for reducing the accumulation of RAN proteins in a subject, biological sample, tissue, or cell. In certain embodiments, the kits and instructions provide for modulating (e.g., reducing or inhibiting) RAN protein translation in a subject, biological sample, tissue, or cell. A kit described herein may include one or more additional pharmaceutical agents described herein as a separate composition.

In some embodiments, other modulators of eIF2, eIF2A, and/or PKR (e.g., proteins, small molecules, nucleic acids, etc.) are formulated as a pharmaceutical composition as described above.

Methods of Treating Diseases and Disorders Associated with RAN Protein Translation or Accumulation In some embodiments, compositions and methods described by the disclosure are useful for reducing or inhibiting RAN protein translation or accumulation in a cell or a subject (e.g., a subject having a disorder or disease associated with RAN translation). In some embodiments, a cell is in vitro. In some embodiments, a subject is a mammalian subject. In some embodiments, a subject is a human subject.

In some aspects, the disclosure provides a method of treating a disease associated with repeat non-ATG protein (RAN protein) translation by administering to a subject expressing a repeat non-ATG protein (RAN protein) an effective amount of a eukaryotic initiation factor 2 (eIF2) modulating agent or an effective amount of a PKR modulating agent (e.g., a PKR inhibitor).

In some embodiments, the eIF2 modulating agent is an inhibitor of PKR. In some embodiments, the inhibitor of PKR is a compound of Formula (I),

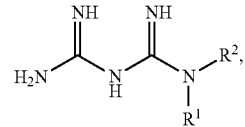

or a pharmaceutically acceptable salt, solvate, hydrate, tautomer, stereoisomer, derivative, or prodrug thereof, wherein: $R^1$ is hydrogen, optionally substituted alkyl, or a nitrogen protecting group; and $R^2$ is hydrogen, optionally substituted alkyl, or a nitrogen protecting group. In some embodiments, the compound of Formula (I) is metformin, buformin, or phenformin.

In some embodiments, the disease associated with repeat non-ATG protein (RAN protein) translation is Huntington's disease (HD, HDL2), Fragile X Syndrome (FRAXA), Spinal Bulbar Muscular Atrophy (SBMA), Dentatorubropallidoluysian Atrophy (DRPLA), Spinocerebellar Ataxia 1 (SCA1), Spinocerebellar Ataxia 2 (SCA2), Spinocerebellar Ataxia 3 (SCA3), Spinocerebellar Ataxia 6 (SCA6), Spinocerebellar Ataxia 7 (SCA7), Spinocerebellar Ataxia 8 (SCA8), Spinocerebellar Ataxia 12 (SCA12), or Spinocerebellar Ataxia 17 (SCA17), amyotrophic lateral sclerosis (ALS), Spinocerebellar ataxia type 36 (SCA36), Spinocerebellar ataxia type 29 (SCA29), Spinocerebellar ataxia type 10 (SCA10), myotonic dystrophy type 1 (DM1), myotonic dystrophy type 2 (DM2), or Fuch's Corneal Dystrophy (e.g., CTG181).

As used herein, an "effective amount" is a dosage of a therapeutic agent sufficient to provide a medically desirable result, such as treatment or amelioration of one or more signs or symptoms caused by a disease or disorder associated with RAN protein translation or accumulation (e.g., a neurodegenerative disease). The effective amount will vary with the age and physical condition of the subject being treated, the severity of the disease or disorder (e.g., the amount of RAN protein accumulation, or cellular toxicity caused by such an accumulation) in the subject, the duration of the treatment, the nature of any concurrent therapy, the specific route of administration and the like factors within the knowledge and expertise of the health practitioner. In some embodiments, an effective amount is the amount of an eIF2α inhibitor, eIF2A inhibitor, or PKR inhibitor that is sufficient to reduce phosphorylation of eIF2α, expression or activity of eIF2A, or any combination thereof.

In some embodiments, methods for treating a disease associated with repeat non-ATG protein (RAN protein) translation described by the disclosure further comprise administering to the subject one or more additional therapeutic agents. The identification and selection of appropriate additional therapeutic agents is within the capabilities of a person of ordinary skill in the art, and will depend upon the disease from which the subject is suffering. For example, in some embodiments one or more therapeutic agents for Huntington's disease (e.g., tetrabenazine, amantadine, chlorpromazine, etc.), Fragile X Syndrome (e.g., selective serotonin reuptake inhibitors, carbamazepine, methylphenidate, Trazodone, etc.), Spinocerebellar Ataxia (e.g., baclofen, riluzole, amantadine, varenicline, etc.), or amyotrophic lateral sclerosis (ALS) (e.g., riluzole, etc.), myotonic dystrophy type 1 (tideglusib, mexiletine, etc.) are administered to the subject.

In some embodiments, an additional therapeutic agent is an antibody that binds specifically to a RAN repeat expansion or antibody that binds specifically to a unique region of a RAN protein that is C-terminal to the repeat expansion. For example, in some embodiments, the antibody binds specifically to a poly-Ser RAN repeat expansion. In some embodiments, the antibody binds to a C-terminal region of a protein comprising a poly-Ser RAN repeat expansion. In some embodiments, an anti-RAN antibody binds to an intracellular RAN protein. In some embodiments, an anti-RAN antibody binds to an extracellular RAN protein.

An anti-RAN antibody can be a polyclonal antibody or a monoclonal antibody. Typically, polyclonal antibodies are produced by inoculation of a suitable mammal, such as a mouse, rabbit or goat. Larger mammals are often preferred as the amount of serum that can be collected is greater. Typically, an antigen (e.g., an antigen comprising a poly-Ser repeat region) is injected into the mammal. This induces the B-lymphocytes to produce IgG immunoglobulins specific for the antigen. This polyclonal IgG is purified from the mammal's serum. Monoclonal antibodies are generally produced by a single cell line (e.g., a hybridoma cell line). In some embodiments, an anti-RAN antibody is purified (e.g., isolated from serum).

Numerous methods may be used for obtaining anti-RAN antibodies. For example, antibodies can be produced using recombinant DNA methods. Monoclonal antibodies may also be produced by generation of hybridomas (see e.g., Kohler and Milstein (1975) Nature, 256: 495-499) in accordance with known methods. Hybridomas formed in this manner are then screened using standard methods, such as enzyme-linked immunosorbent assay (ELISA) and surface plasmon resonance (e.g., OCTET or BIACORE) analysis, to identify one or more hybridomas that produce an antibody that specifically binds with a specified antigen. Any form of the specified antigen (e.g., a RAN protein) may be used as the immunogen, e.g., recombinant antigen, naturally occurring forms, any variants or fragments thereof. One exemplary method of making antibodies includes screening protein expression libraries that express antibodies or fragments thereof (e.g., scFv), e.g., phage or ribosome display libraries. Phage display is described, for example, in Ladner et al., U.S. Pat. No. 5,223,409; Smith (1985) Science 228:1315-1317; Clackson et al. (1991) Nature, 352: 624-628; Marks et al. (1991) J. Mol. Biol., 222: 581-597WO92/18619; WO 91/17271; WO 92/20791; WO 92/15679; WO 93/01288; WO 92/01047; WO 92/09690; and WO 90/02809.

Administration of a treatment may be accomplished by any method known in the art (see, e.g., Harrison's Principle of Internal Medicine, McGraw Hill Inc.). Administration may be local or systemic. Administration may be parenteral (e.g., intravenous, subcutaneous, or intradermal) or oral. Compositions for different routes of administration are well known in the art (see, e.g., Remington's Pharmaceutical Sciences by E. W. Martin). Dosage will depend on the subject and the route of administration. Dosage can be determined by the skilled artisan.

Routes of administration include but are not limited to oral, parenteral, intravenous, intramuscular, intraperitoneal, intranasal, sublingual, intratracheal, inhalation, subcutaneous, ocular, vaginal, and rectal. Systemic routes include oral and parenteral. Several types of devices are regularly used for administration by inhalation. These types of devices include metered dose inhalers (MDI), breath-actuated MDI, dry powder inhaler (DPI), spacer/holding chambers in combination with MDI, and nebulizers.

In some embodiments, a treatment for a disease associated with RAN protein expression is administered to the central nervous system (CNS) of a subject in need thereof. As used herein, the "central nervous system (CNS)" refers to all cells and tissues of the brain and spinal cord of a subject, including but not limited to neuronal cells, glial cells, astrocytes, cerebrospinal fluid, etc. Modalities of administering a therapeutic agent to the CNS of a subject include direct injection into the brain (e.g., intracerebral injection, intraventricular injection, intraparenchymal injection, etc.), direct injection into the spinal cord of a subject (e.g., intrathecal injection, lumbar injection, etc.), or any combination thereof.

In some embodiments, a treatment as described by the disclosure is systemically administered to a subject, for example by intravenous injection. Systemically administered therapeutic molecules (e.g., eIF2 modulating agents, PKR inhibitors, etc.) can be modified, in some embodiments, in order to improve delivery of the molecules to the CNS of a subject. Examples of modifications that improve CNS delivery of therapeutic molecules include but are not limited to co-administration or conjugation to blood brain barrier-targeting agents (e.g., transferrin, melanotransferrin, low-density lipoprotein (LDL), angiopeps, RVG peptide, etc., as disclosed by Georgieva et al. *Pharmaceuticals* 6(4): 557-583 (2014)), coadministration with BBB disrupting agents (e.g., bradykinins), and physical disruption of the BBB prior to administration (e.g., by MRI-Guided Focused Ultrasound), etc.

An eIF2 modulating agent may be delivered by any suitable modality known in the art. In some embodiments, an eIF2 modulating agent is delivered to a subject by a vector, such as a viral vector (e.g., adenovirus vector, recombinant adeno-associated virus vector (rAAV vector), lentiviral vector, etc.) or a plasmid-based vector.

In some aspects, the disclosure is based on the discovery that, in some embodiments, administration of a recombinant adeno-associated virus (rAAV) comprising a transgene encoding an eIF2α modulating agent to a subject (e.g., a subject having a disease characterized by translation and accumulation of RAN proteins) reduces RAN protein translation and RAN protein aggregation in the subject.

In some embodiments, a recombinant rAAV particle comprises a nucleic acid vector, such as a single-stranded (ss) or self-complementary (sc) AAV nucleic acid vector. In some embodiments, the nucleic acid vector comprises a transgene encoding an eIF2 modulating agent as described herein, and one or more regions comprising inverted terminal repeat (ITR) sequences (e.g., wild-type ITR sequences or engineered ITR sequences) flanking the expression construct. In some embodiments, the nucleic acid is encapsidated by a viral capsid. In some embodiments, the transgene is operably linked to a promoter, for example a constitutive promoter or an inducible promoter. In some embodiments, the promoter is a tissue-specific (e.g., CNS-specific) promoter.

Accordingly, in some embodiments, a rAAV particle comprises a viral capsid and a nucleic acid vector as described herein, which is encapsidated by the viral capsid. In some embodiments, the viral capsid comprises 60 capsid protein subunits comprising VP1, VP2 and VP3. In some embodiments, the VP1, VP2, and VP3 subunits are present in the capsid at a ratio of approximately 1:1:10, respectively.

The ITR sequences of a nucleic acid or nucleic acid vector described herein can be derived from any AAV serotype (e.g., 1, 2, 3, 4, 5, 6, 7, 8, 9, or 10) or can be derived from more than one serotype. In some embodiments of the nucleic acid or nucleic acid vector provided herein, the ITR sequences are derived from AAV2. ITR sequences and plasmids containing ITR sequences are known in the art and commercially available (see, e.g., products and services available from Vector Biolabs, Philadelphia, Pa.; Cellbiolabs, San Diego, Calif.; Agilent Technologies, Santa Clara, Ca; and Addgene, Cambridge, Mass.; and Gene delivery to skeletal muscle results in sustained expression and systemic delivery of a therapeutic protein. Kessler P D, Podsakoff G M, Chen X, McQuiston S A, Colosi P C, Matelis L A, Kurtzman G J, Byrne B J. Proc Natl Acad Sci USA. 1996 Nov. 26; 93(24):14082-7; and Curtis A. Machida. Methods in Molecular Medicine™. Viral Vectors for Gene Therapy Methods and Protocols. 10.1385/1-59259-304-6:201 © Humana Press Inc. 2003. Chapter 10. Targeted Integration by Adeno-Associated Virus. Matthew D. Weitzman, Samuel M. Young Jr., Toni Cathomen and Richard Jude Samulski; U.S. Pat. Nos. 5,139,941 and 5,962,313, all of which are incorporated herein by reference). An exemplary AAV2 ITR sequence is shown below.

(SEQ ID NO: 14)
TTGGCCACTCCCTCTCTGCGCGCTCGCTCGCTCACTGAGGCCGGGCGACCA

AAGGTCGCCCGACGCCCGGGCTTTGCCCGGGCGGCCTCAGTGAGCGAGCGA

GCGCGCAGAGAGGGAGTGGCCAACTCCATCACTAGGGGTTCCT

In some embodiments, the expression construct is no more than 7 kilobases, no more than 6 kilobases, no more than 5 kilobases, no more than 4 kilobases, or no more than 3 kilobases in size. In some embodiments, the expression construct is between 4 and 7 kilobases in size.

The rAAV particle may be of any AAV serotype (e.g., 1, 2, 3, 4, 5, 6, 7, 8, 9, or 10), including any derivative (including non-naturally occurring variants of a serotype) or pseudotype. In some embodiments, the rAAV particle is an rAAV9 particle. Additional AAV serotypes and derivatives/pseudotypes, and methods of producing such derivatives/pseudotypes are known in the art (see, e.g., Mol Ther. 2012 April; 20(4):699-708. doi: 10.1038/mt.2011.287. Epub 2012 Jan. 24. The AAV vector toolkit: poised at the clinical crossroads. Asokan A1, Schaffer D V, Samulski R J.).

These and other aspects of the application are illustrated by the following non-limiting examples.

EXAMPLES

Figure 1B:
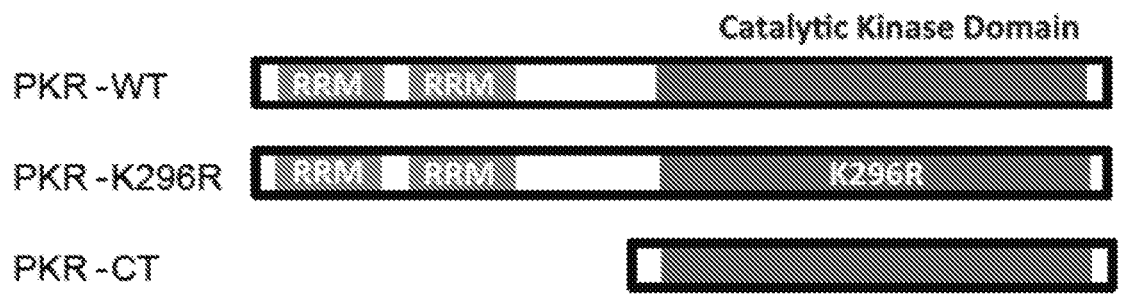

Example 1: Protein Kinase R (PKR) Regulates RAN Translation of CAG, CCTG, G4C2 Expansions Through eIF2a-P Pathway Diagrams of CAG, CCTG and GGGCC repeat expansion constructs used to test effects of protein kinase R (PKR) on repeat associated non-ATG (RAN) translation are shown in FIG. 1A. Briefly, constructs have a 6× stop-codon cassette (e.g., two stops in each reading frame, upstream of the repeat expansions and C-terminal epitope tags). A diagram of PKR vectors expressing wildtype (PKR-WT), the dominant negative K296R mutant form of PKR (PKR-K296R), or the C-terminal only domain (PKR-CT) are shown in FIG. 1B.

Figure 1C:
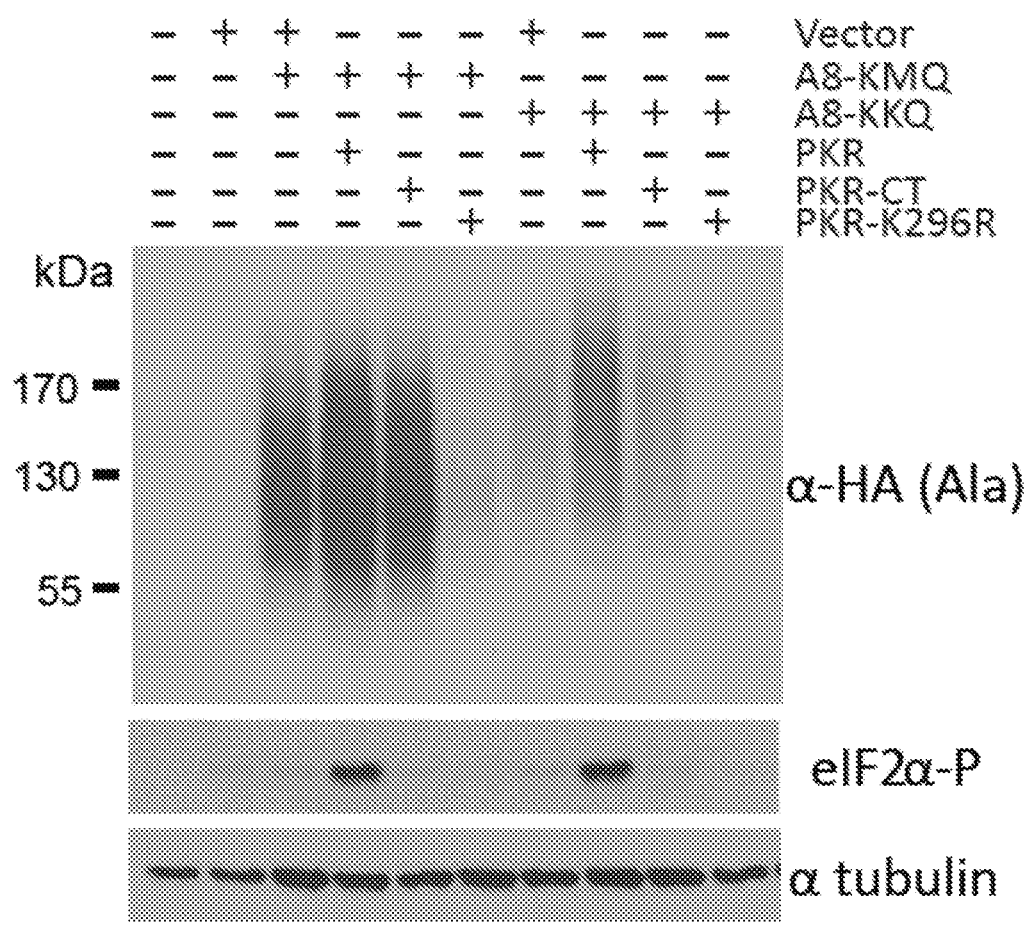

HEK293T cells were transfected with RAN protein-expressing and PKR-expressing constructs. Immunoblot analysis indicated that PKR-WT increases polyAla RAN protein from CAG expansion constructs, PKR-CT lacking the RRM motifs has no effect on polyAla RAN levels, and the dominant negative mutant K296R PKR decreases polyAla RAN levels (FIG. 1C). The immunoblot also indicated that PKR increases levels of eIF2α-P, PKR-CT has no effect and PKR K296R decreases steady state levels of eIF2α-P.

Figure 1D:
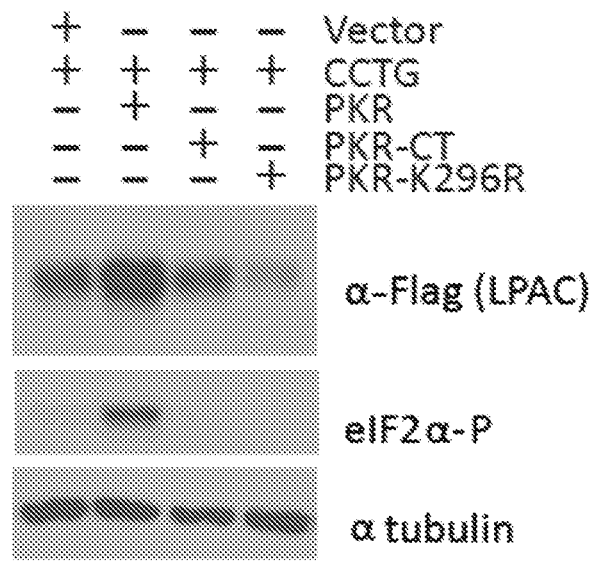

Immunoblot analysis indicated that PKR-WT increases poly Leu-Pro-Ala-Cys (polyLPAC) RAN protein from CCTG expansion construct, PKR-CT has no effect on LPAC RAN levels, and the dominant negative mutant K296R PKR decreases polyLPAC RAN levels (FIG. 1D). It was also observed that PKR-CT has no effect, and PKR K296R decreases steady state levels of eIF2α-P.

Figure 1E:
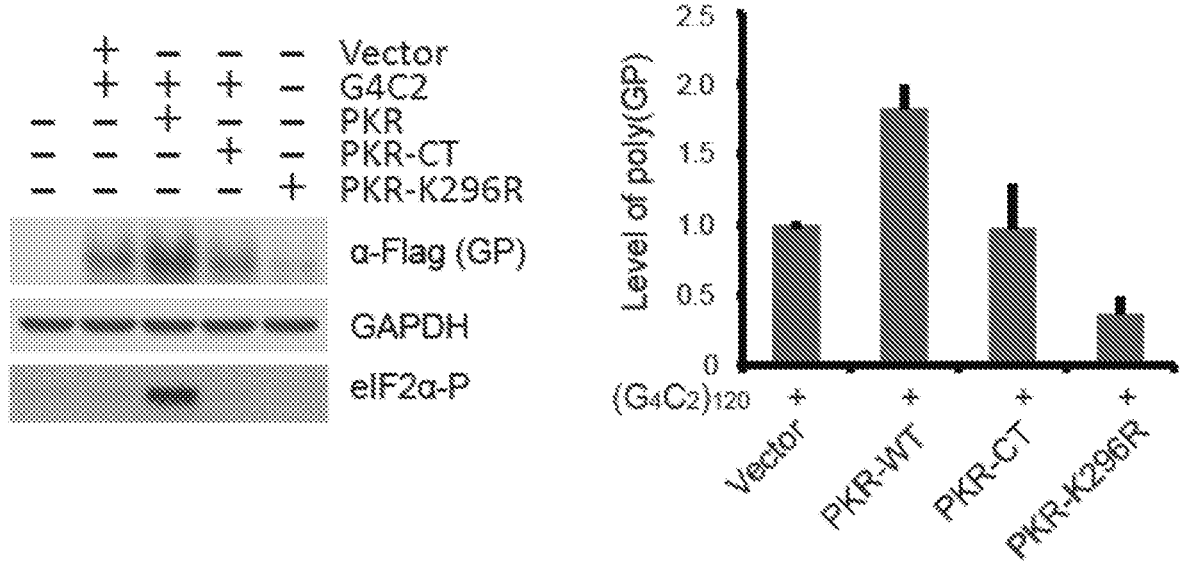

Immunoblot analysis indicated that PKR-WT increases, PKR-CT has no effect, and mutant K296R PKR decreases polyGP RAN protein levels, and that PKR increases, PKR-CT has no effect and PKR K296R decreases steady state levels of eIF2α-P (FIG. 1E).

eIF2α-P Increases RAN Protein Levels in HEK293T Cells.

Figure 2A:
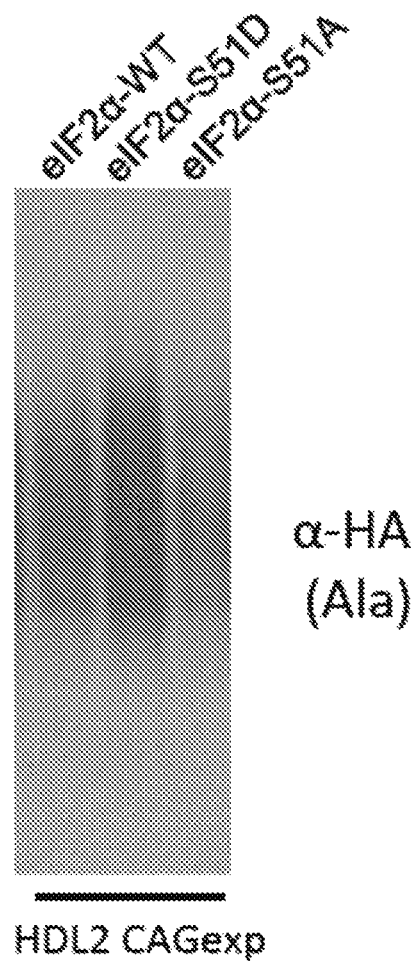
FIGS. 2A-2C show eIF2α-P increases RAN protein levels in HEK293T cells.
Figure 2B:
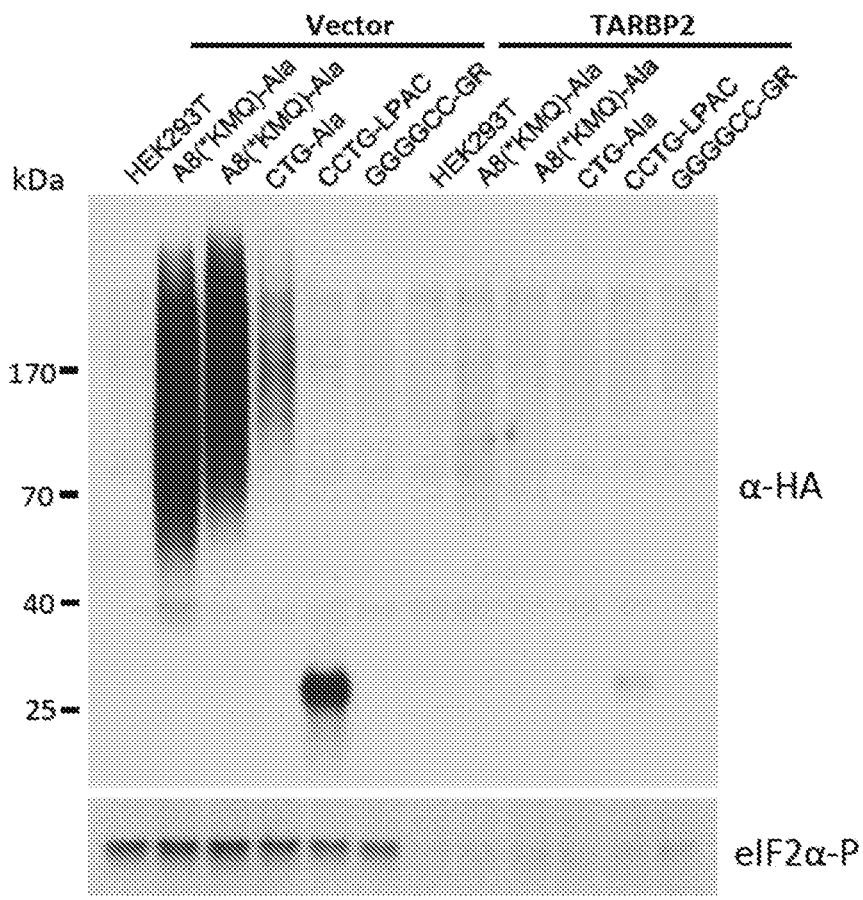
Figure 2C:
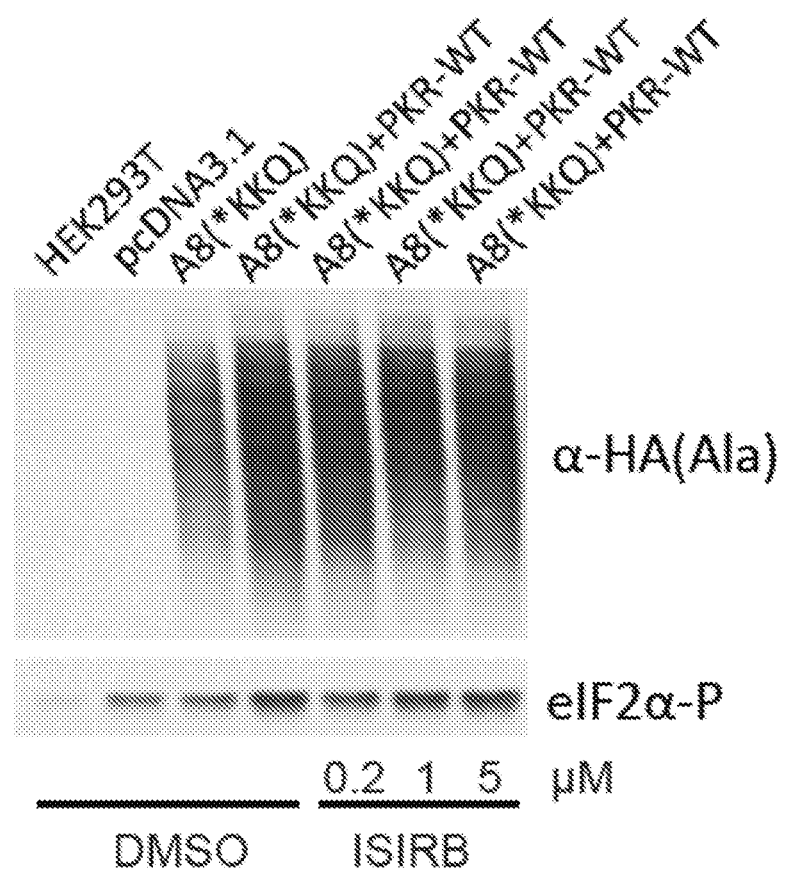

The effect of eIF2α phosphorylation on RAN protein translation was investigated. Protein blots of HEK293T cells co-transfected with plasmids expressing WT or mutant eIF2α and a CAG expansion (CAGexp) show increased polyAla RAN protein levels in cells overexpressing the phosphomimetic eIF2α-S51D mutation compared to eIF2α-WT or the non-phosphorylatable eIF2α-S51A (FIG. 2A). It was observed that polyAla, polyAla and LPAC RAN proteins expressed from CAG, CTG and CCTG repeat expansions respectively, decrease in the presence of a PKR inhibitor (TARBP2) which reduces levels of eIF2α-P (FIG. 2B). It was also observed that polyAla RAN protein levels decrease in the presence of ISIRB, which inhibits downstream effects of eIF2α-P (FIG. 2C).

Inhibition of PKR Pathway Decreases RAN Protein Aggregates and Improves Behavioral Phenotype in C9-500 BAC Transgenic Mice.

Figure 3A:
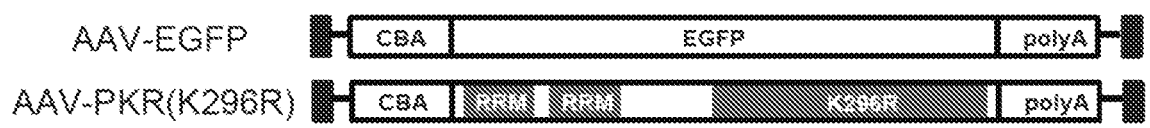
FIGS. 3A-3C show inhibition of PKR pathway decreases RAN protein aggregates and improves behavioral phenotype in C9-500 BAC transgenic mice.

Schematic diagrams of AAV2/9 constructs used for rAAV injections into a BAC transgenic mouse model of C9orf72 ALS/FTD containing 500 G4C2 repeats (C9-500 BAC) are shown in FIG. 3A. Briefly, animals were sacrificed for analysis at 3 months of age after postnatal day 1 (P1) intracerebral ventricular (ICV) injections with AAV2/9 virus expressing either EGFP or the dominant negative form of PKR(K296R).

Figure 3B:
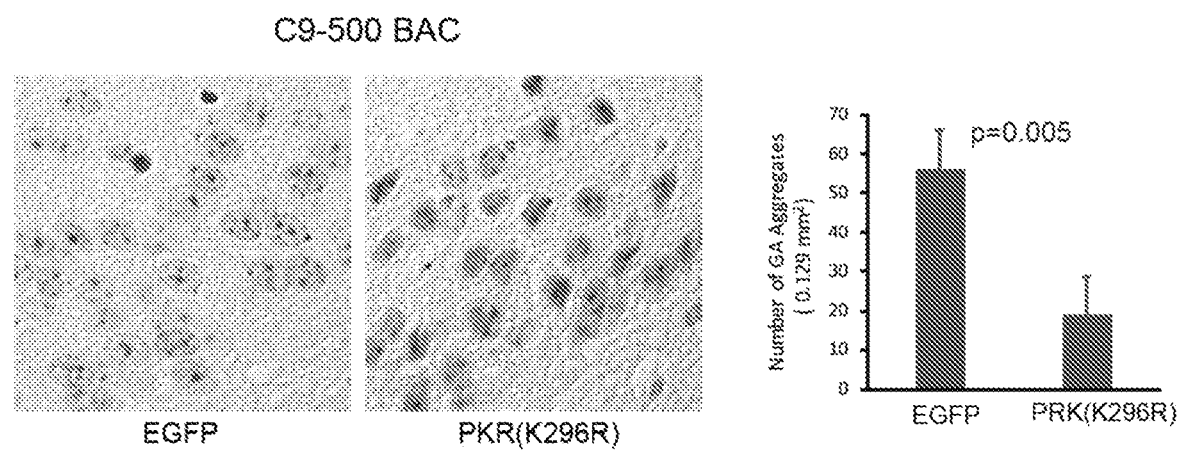
Figure 3C:
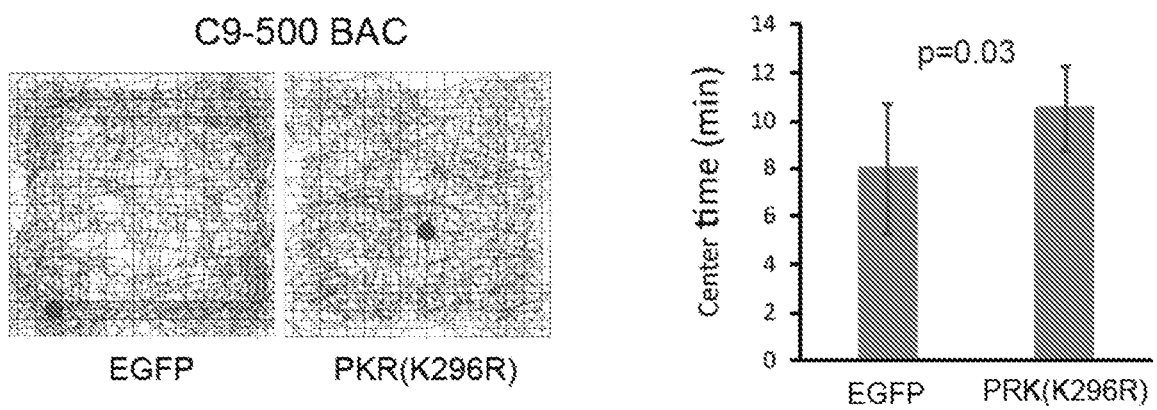

Representative immunohistochemical (IHC) staining of GA RAN protein aggregates in sections of the retrosplenial cortex from C9-500 BAC mice (FIG. 3B, left). Quantification of GA RAN protein aggregates was also performed (FIG. 3B, right). Analysis was done in a blinded fashion. Data indicated that animals treated with the dominant negative mutant PKR(K296R) have fewer GA RAN protein aggregates compared to age matched EGFP control animals. Openfield analysis was also performed (FIG. 3C) and indicated that C9-500 BAC animals treated with dominant negative PKR(K296R) show reduced center time, a phenotype indicative of anxiety-like behavior compared to EGFP control animals.

Figure 4:
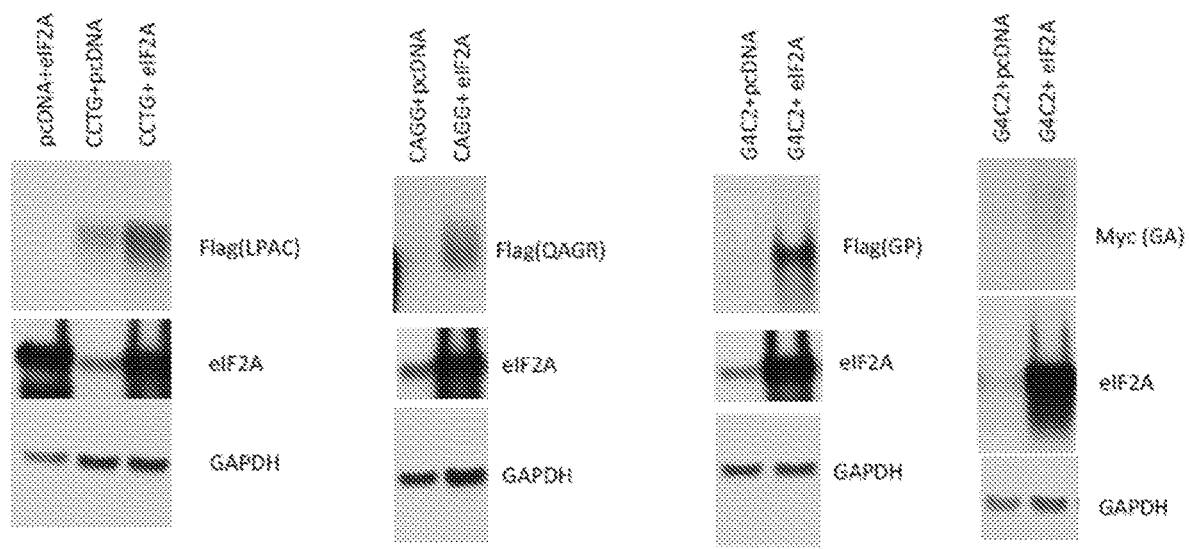
FIG. 4 shows the alternative eIF2A initiation factor increases RAN translation. eIF2A is an alternative eukaryotic translation initiation factor that can be used under specific conditions as an alternative to eIF2α. Constructs used to express RAN proteins are shown with a 6× stop codon (2 upstream stop codons in each reading frame) a repeat expansion mutation (CCTG, CAGG or GGGCC) and a 3' triple tag with epitope tags in each reading frame. Co-transfections with these repeat expansion constructs, in combination with overexpression of eIF2A, increases RAN protein levels, demonstrating that eIF2A can serve as an alternative eukaryotic initiation factor for RAN across a variety of disease causing expansion mutations.

The Alternative eIF2A Initiation Factor Increases RAN Translation.

eIF2A is an alternative eukaryotic translation initiation factor that, in some embodiments, can be used under specific conditions as an alternative to eIF2α. Typically, phosphorylation of eIF2α prevents its use in translational initiation and RAN translation increases under conditions favoring eIF2α-P. Therefore, whether eIF2A can serve as an alternative initiation factor for RAN translation was investigated. Constructs used to express RAN proteins are shown (FIG. 4). Co-transfections with the repeat expansion constructs, in combination with overexpression of eIF2A, increased RAN protein levels, indicating that eIF2A can serve as an alternative eukaryotic initiation factor for RAN across a variety of disease causing expansion mutations. These data also identify eIF2A as a novel drug target to modulate RAN protein levels.

eIF2α phosphorylation, which Downregulates Global Translation Leads to Increased RAN Protein Levels.

Generally, four major stress pathways (PKR, heme-regulated inhibitor (HRI), general control nonderepressible (GCN), and Protein kinase RNA-like endoplasmic reticulum kinase (PERK)) that lead to eIF2α phosphorylation (eIF2α-P) and repression of global protein synthesis. Surprisingly, it was observed that conditions that favor eIF2α-P lead to upregulation of RAN translation across multiple types of repeats.

In some embodiments, when disease causing repeat expansion mutations are expressed, hairpin forming double stranded RNAs (dsRNA) and/or dsRNAs from expression of sense and antisense transcripts are produced. In some embodiments, these mutant dsRNAs lead to a chronic over activation of the PKR pathway. In some embodiments, chronic activation of the PKR pathway leads to eIF2α phosphorylation, the use of the alternative initiation factor eIF2A, and increased RAN translation.

As described in the Examples above, it was observed that RAN translation is upregulated by PKR overexpression and substantially reduced by overexpression of a dominant negative form of PKR which blocks eIF2α-P from the PKR pathway. It was also observed that RAN proteins levels increase with increased levels of eIF2α phosphorylation and decrease with inhibitors of eIF2α phosphorylation including TARDBP2. It was also observed that the alternative initiation factor eIF2A, increases RAN protein levels. In some embodiments, this alternative eukaryotic initiation factor (e.g., eIF2A) can be used under stress conditions when eIF2α phosphorylation prevents canonical translation initiation with eIF2α. In some embodiments, because eIF2A does not require an AUG initiation codon, it allows translation initiation at multiple types of non-AUG start codons which is a feature of RAN translation.

Figure 5:
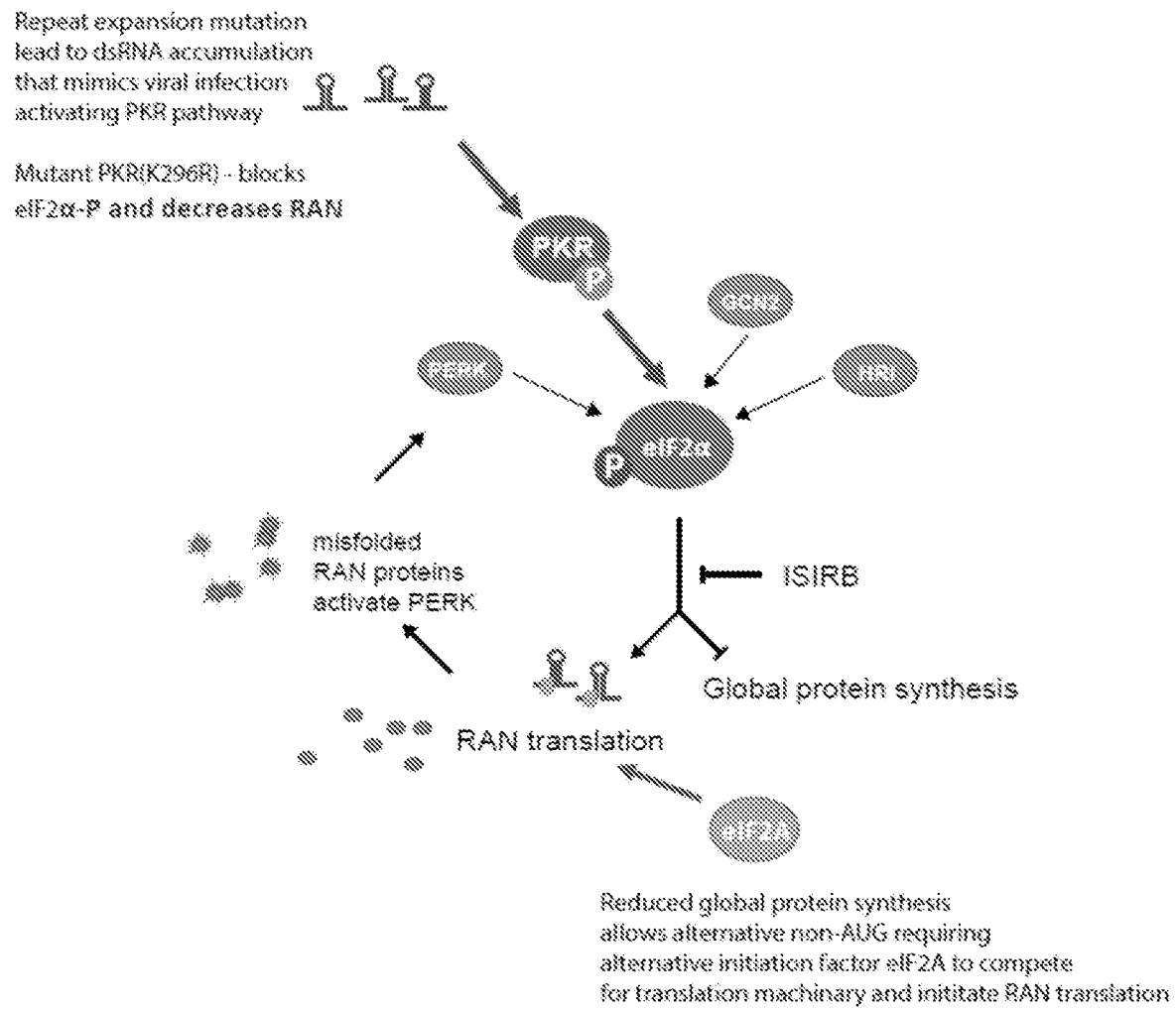
FIG. 5 shows a schematic diagram showing eIF2a phosphorylation, which downregulates global translation, leads to increased RAN protein levels.

In summary, stress pathways have been identified as critical drivers of RAN translation, and as druggable targets that can be used to modulate RAN translation in disease, including but not limited to C9orf72 ALS/FTD (G4C2 and G2C4 repeats), myotonic dystrophy type 1, Huntington's disease and multiple forms of spinocerebellar ataxia (CAG and CTG repeats), and myotonic dystrophy type 2 (CCTG and CAGG repeats). Data indicate that inhibition of the PKR or eIF2α pathways decreases RAN protein accumulation. eIF2A has also been identified as an alternative eukaryotic initiation factor. FIG. 5 shows a schematic diagram showing eIF2α phosphorylation, which downregulates global translation, leads to increased RAN protein levels.

Example 2: Metformin Inhibits RAN Translation Though PKR Pathway and Ameliorates Phenotypes in a C9orf72 Mouse Model This Example describes activation of the PKR pathway by structured RAN-positive repeat expansion RNAs. In some embodiments, the activation leads to increased phospho-eIF2α (p-eIF2α) and increased RAN protein levels. It was observed that inhibition of PKR decreased RAN protein levels in cell culture and a BAC transgenic mouse model of C9orf72 ALS/FTD (C9-BAC). It was also observed that metformin (and certain metformin derivatives, for example buformin and phenformin) inhibits phospho-PKR activation, decreases RAN protein levels and improves phenotypes in C9-BAC mice.

Materials and Methods

Cell Culture and Transfection

HEK293T cells were cultured in DMEM medium supplemented with 10% fetal bovine serum and incubated at 37° C. in a humid atmosphere containing 5% $CO_2$. DNA transfections were performed using Lipofectamine 2000 Reagent (Invitrogen) according to the manufacturer's instructions.

AAV Construction and Preparation

AAV vectors expressing the PKR under the control of the cytomegalovirus enhance/chicken beta actin (CBA) promoter, a woodchuck hepatitis virus post-transcriptional-regulatory element (WPRE), and the bovine growth hormone polyA were generated by Polyethylenimine Linear (PEI, Polysciences) transfection into HEK293T cells. Cells were co-transfected with AAV helper plasmids pDP8.ape to produce recombinant adeno-associated viral (rAAV) vector rAAV2/8.

Intracerebroventricular (ICV) Injection

Neonatal pups were injected within 0-12 hours after birth. The naive pups were covered in aluminum foil and completely surrounded in ice for 3-4 minutes, resulting in the body temperature being lowered to <10° C. The pups were considered completely cryoanesthetized when all movement stops and the skin color changes from pink to purple. 2 al of virus (1013 viral genomes/ml) was slowly injected into the ventricle using 10 al syringes (30 degree beveled). After injection pups were allowed to completely recover on a warming blanket and then returned to the home cage.

Immunofluorescence

The subcellular distribution of polymeric proteins was assessed in transfected HEK293T cells by immunofluorescence. Cells were plated on 8 well tissue-culture chambers and transfected with plasmids the next day. Forty-eight hours post-transfection, cells were fixed in 4% paraformaldehyde (PFA) in PBS for 30 min and permeabilized in 0.5% triton X-100 in PBS for 15 min on ice. The cells were blocked in 1% normal goat serum (NGS) in PBS for 30 min. After blocking, the cells were incubated for 1 hour at RT in blocking solution containing the rabbit anti-Myc (Abcam), mouse anti-HA (Covance), mouse anti-Flag (Sigma), rabbit α-GR and rabbit α-GR-CT primary antibodies at a dilution of 1:400. The slides were washed three times in PBS and incubated for 1 hour at RT in blocking solution containing Goat anti-rabbit conjugated to Cy3 (Jackson ImmunoResearch, PA) and goat anti-mouse conjugated to Alexa Fluor 488 (Invitrogen) secondary antibodies at a dilution of 1:200. The slides were washed three times in PBS and mounted with mounting medium containing DAPI (Invitrogen). Immunofluorescence in patient hippocampal tissue was performed on the 6 am fresh frozen sections. A similar protocol was used as in transfected cells, except 2% NGS was used as blocking buffer and higher dilution of antibodies was used (mouse α-GP 1:1000 and rabbit α-GP-CT 1:5000).

Western Blotting

Transfected cells in each well of a six-well tissue-culture plate were rinsed with PBS and lysed in 300 μL RIPA buffer with protease inhibitor cocktail for 45 min on ice. DNA was sheared by passage through a 21-gauge needle. The cell lysates were centrifuged at 16,000×g for 15 min at 4° C., and the supernatant was collected. The protein concentration of the cell lysate was determined using the protein assay dye reagent (Bio-Rad). Twenty micrograms of protein were separated in a 4-12% NuPAGE Bis-Tris gel (Invitrogen) and transferred to a nitrocellulose membrane (Amersham). The membrane was blocked in 5% dry milk in PBS containing 0.05% Tween-20 (PBS-T) and probed with the anti-Flag (1:2000), anti-Myc (1:1000), anti-HA (1:1000), or rabbit polyclonal antibodies (1:1000) in blocking solution. After the membrane was incubated with anti-rabbit or anti-mouse HRP-conjugated secondary antibody (Amersham), bands were visualized by the ECL plus Western Blotting Detection System (Amersham).

Sequential extraction of patient frontal cortex autopsy tissue was performed as follows: tissue was homogenized in PBS containing 1% Triton-X100, 15 mM $MgCl_2$, 0.2 mg/ml DNase I and protease inhibitor cocktail and centrifuged at 16,000×g for 15 min at 4° C. The supernatant was collected. The pellet was resuspended in 2% SDS and incubated at room temperature for 1 hour, then centrifuged at 16,000×g for 15 min at 4° C. The supernatant was collected and the 2% SDS insoluble pellet was resuspended in 8% SDS, 62.5 mM Tris-HCl pH 6.8, 10% glycerol and 20% 2-Mercaptoethanol for protein blotting.

Figure 6A:
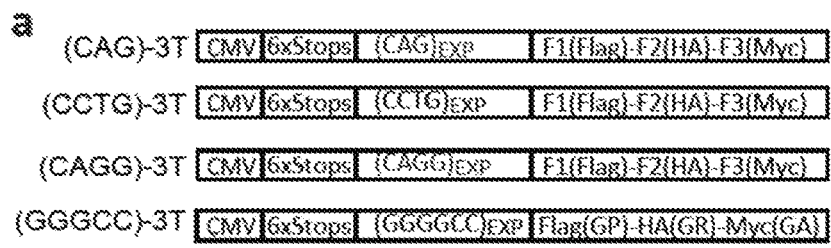
FIGS. 6A-6G show data indicating that Protein kinase R (PKR) regulates RAN translation of CAG, CCTG, CAGG, G4C2 expansions by activating PKR pathway.
Figure 6B:
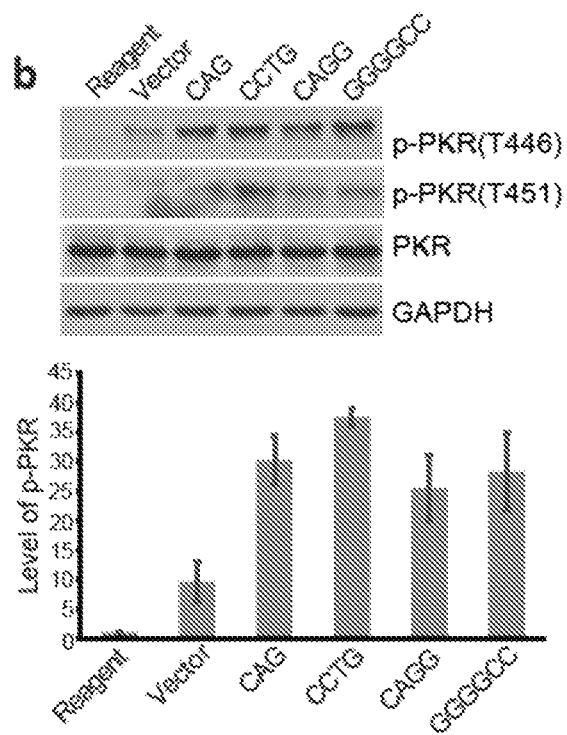

Activation of PKR by Expansion RNAs Induces RAN Translation,

Repeat expansions have been observed to undergo RAN translation. CUG repeats have been observed to activate PKR. Therefore, the ability of other RAN positive repeat expansions to activate PKR and the role of PKR on RAN translation were tested. HEK293T cells expressing CAG, CCUG, CAGG and GGGGCC expansion RNAs (FIG. 6A) were observed to have increased levels of phospho-PKR at sites critical for PKR activation (T446 and T451) (FIG. 6B).

Figure 6C:
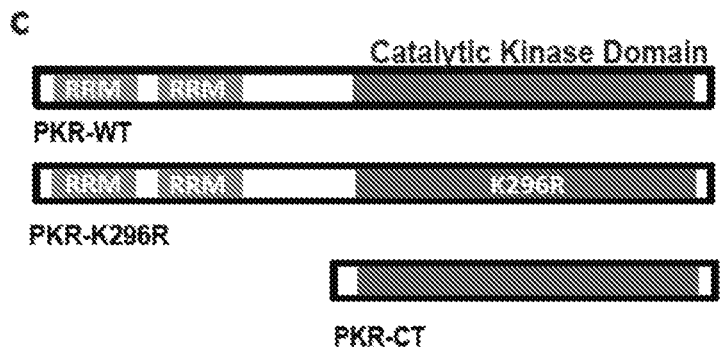
Figure 6D:
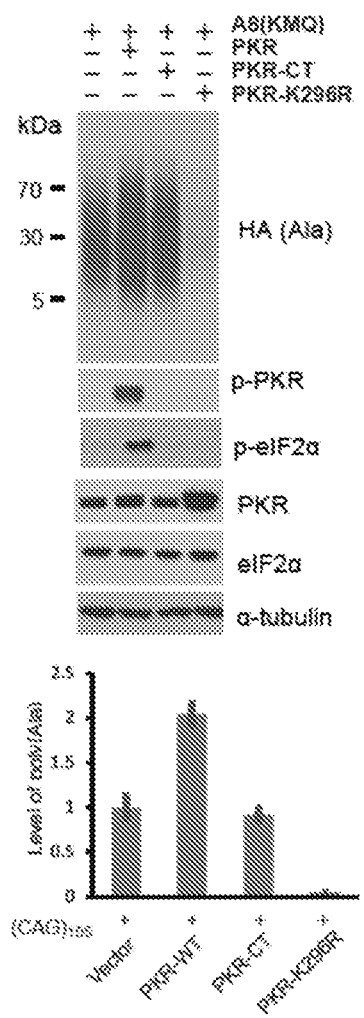
Figure 6E:
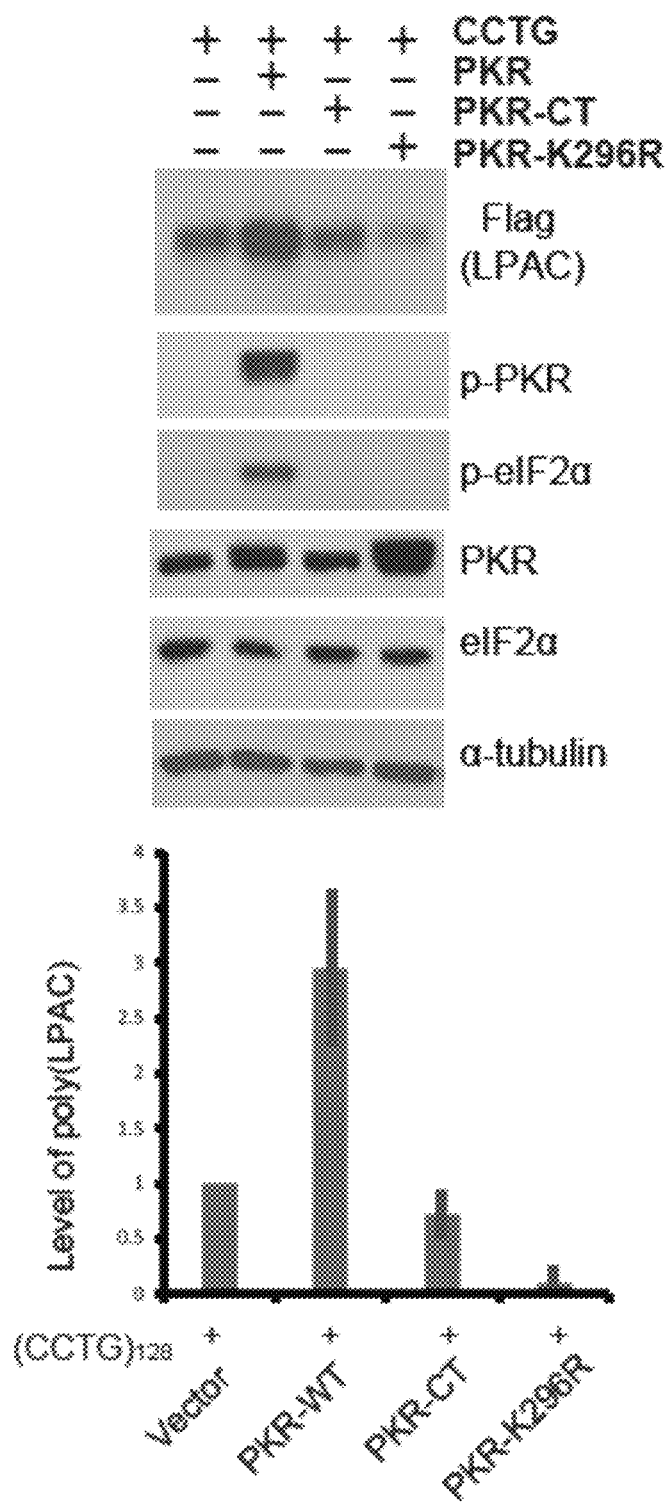
Figure 6F:
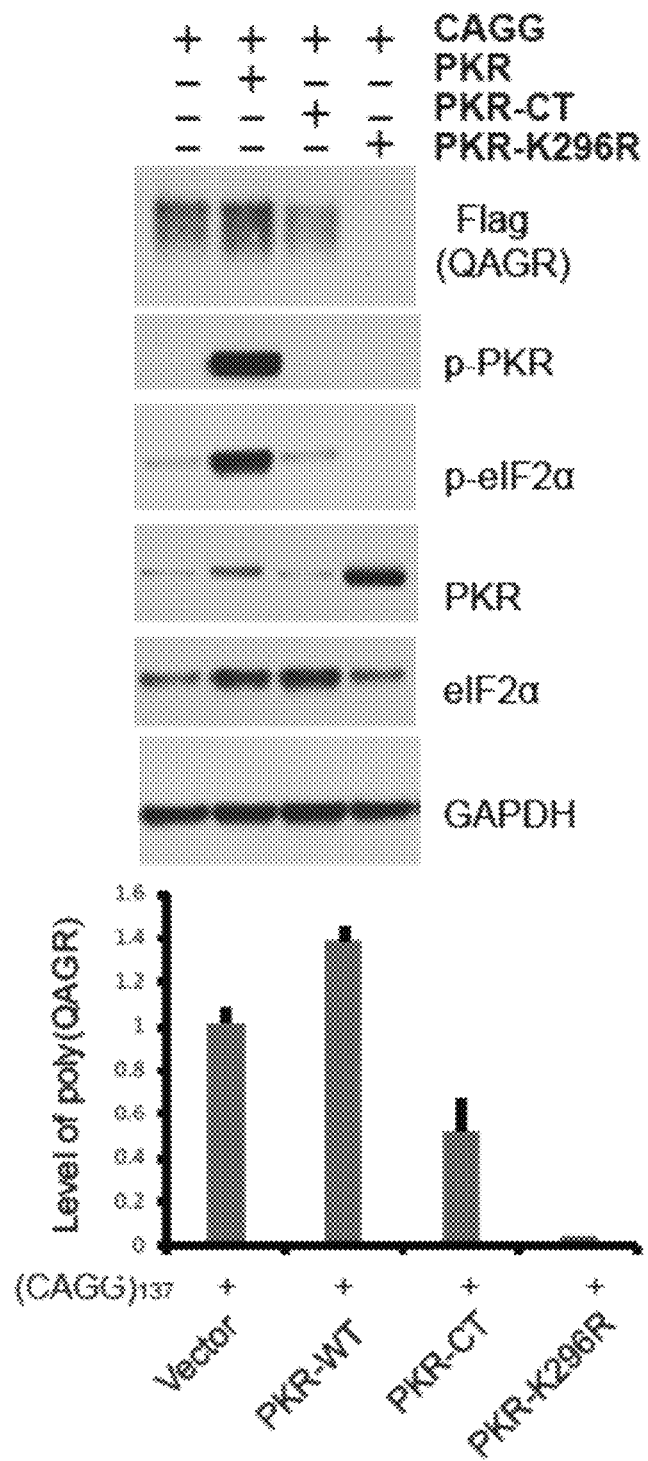
Figure 6G:
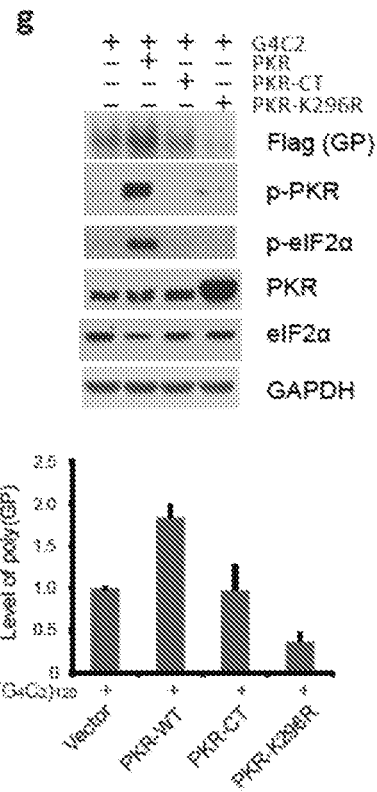
Figure 7A:
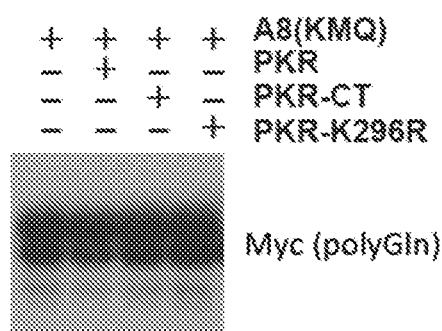
FIGS. 7A-7B show PKR activation decreases LPAC RAN protein in three reading frames but does not affect levels of ATG-initiated polyGlutamine protein.
Figure 7B:
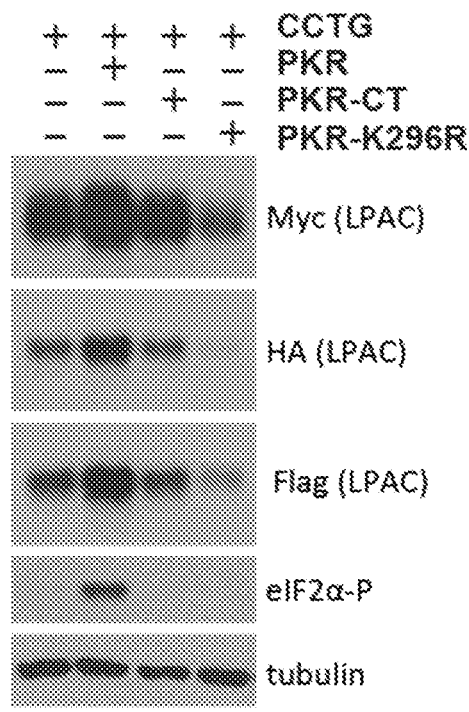

Next, the effects of PKR overexpression and inhibition on RAN protein accumulation across several types of repeat expansions were tested. Plasmids expressing CAG, CCUG, CAGG or GGGGCC repeat expansions were co-transfected with constructs expressing either full-length PKR, a dominant negative form of the enzyme (PKR-K296R), or an inactive PKR lacking the RNA binding domain (PKR-Cter) (FIG. 6C). For $CAG_{EXP}$ expressing cells, PKR-WT overexpression led to increased p-PKR and p-eIF2α, and increased RAN polyAla protein levels. In contrast, expression of the dominant-negative PKR-K296R mutation decreased polyAla RAN protein levels. Expression of the inactive form of the enzyme had no effect (FIG. 6D). The polyGln reading frame, which contains an AUG initiation codon, is not affected by PKR (FIG. 7A).

RAN polyLPAC, polyQAGR and polyGP proteins expressed across CCUG, CAGG and GGGGCC repeats, were increased with PKR-WT overexpression and decreased with PKR-K296R (FIGS. 6E-6G and FIG. 7B). These data indicate that several types of microsatellite expansion mutations activate the PKR pathway, and that PKR regulates RAN protein accumulation.

Upregulation of RAN Translation Through PKR-Mediated Phosphorylation of eIF2α.

Figure 8A:
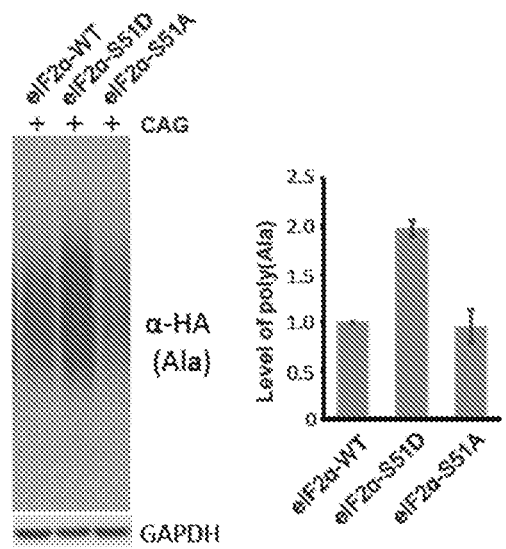
FIGS. 8A-8C show RAN protein levels regulated by PKR/eIF2a pathways.
Figure 8B:
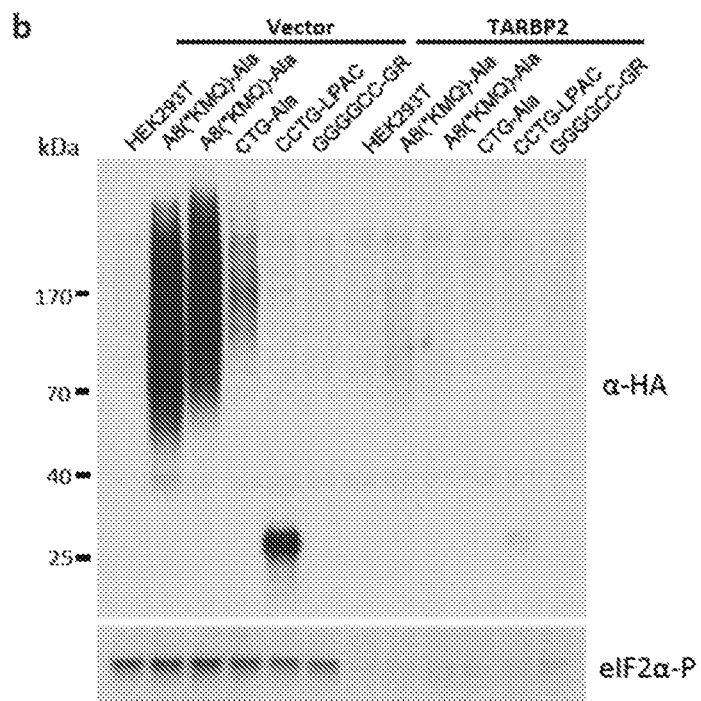

PKR was inhibited by overexpressing the TAR RNA binding protein (also referred to as TRBP or TARBP2). Co-transfection experiments indicate that TARBP2 overexpression decreases levels of RAN polyAla expressed from CAG and CUG expansion RNAs and polyLPAC expressed from CCUG transcripts (FIGS. 8A-8B). In some embodiments, the formation of the terinary complex [eIF2α-GTP/Met-tRNA$_i^{Met}$] is required for AUG-initiated translation. In some embodiments, phosphorylation of eIF2α is a key regulatory mechanism that decreases overall translation under conditions of stress. Consistent with the role of PKR in the integrated stress response pathway, PKR inhibition by TARBP2 was observed to decrease p-eIF2α (FIG. 8B). These data indicate that the regulation of RAN translation is upregulated by expansion-induced PKR activation, through the eIF2α pathway.

To directly test if the eIF2α pathway affects RAN translation HEK293T cells were co-transfected with CAG expansion constructs expressing WT, phosphomimetic (S51D), or a non-phosphorylatable S51A mutant form of eIF2α. Expression of the phosphomimetic form of eIF2α (eIF2α-S51D) was observed to increase steady state levels of polyAla RAN protein, while the non-phosphorylatable eIF2α-S51A mutation had no effect compared to cells expressing WT eIF2α (FIG. 8A).

Figure 8C:
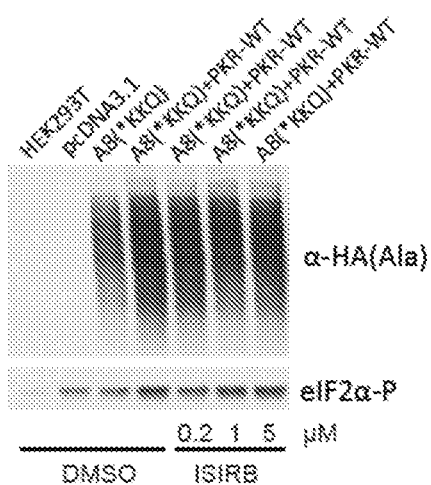

ISRIB has been identified as a potent inhibitor of the ISR pathway inhibitor that decreases the effects of eIF2α phosphorylation and blocks the downstream effects of all eIF2α kinases including PKR. Here, it was observed that ISRIB reduces polyAla RAN protein levels in HEK293T transfected with expanded CAG and PKR-WT constructs (FIG. 8C).

Figure 9:
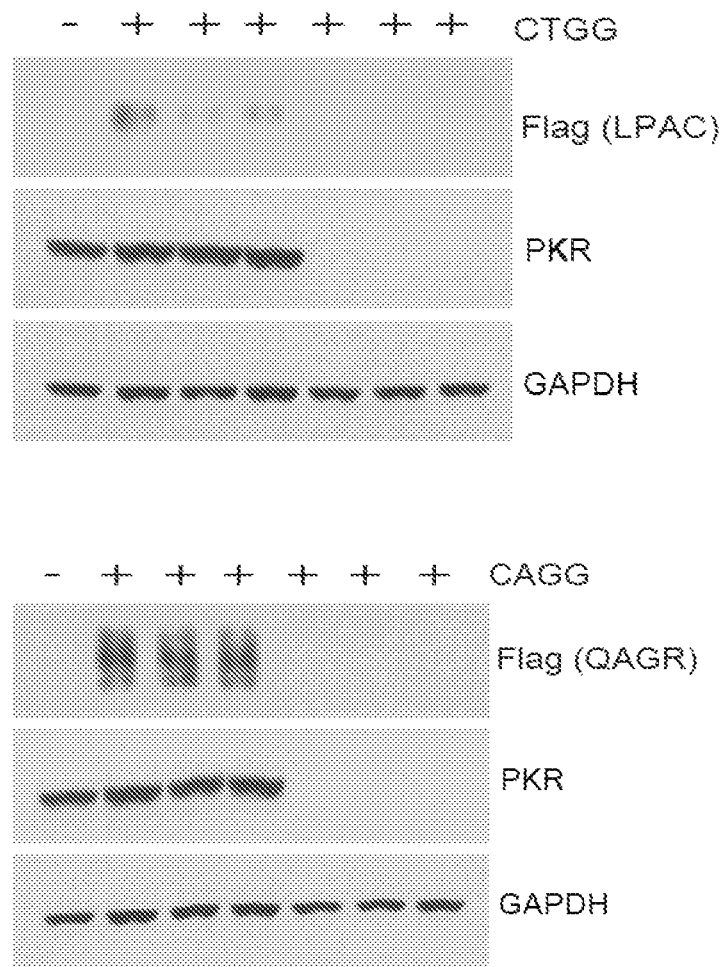
FIG. 9 shows CRISPR/Cas9 knockout of PKR in HEK293T cells. Transient transfections of CAG, CCTG, and CAGG expansion constructs show a reduction of polyAla, polyLPAC, and polyQAGR proteins.
Figure 9:
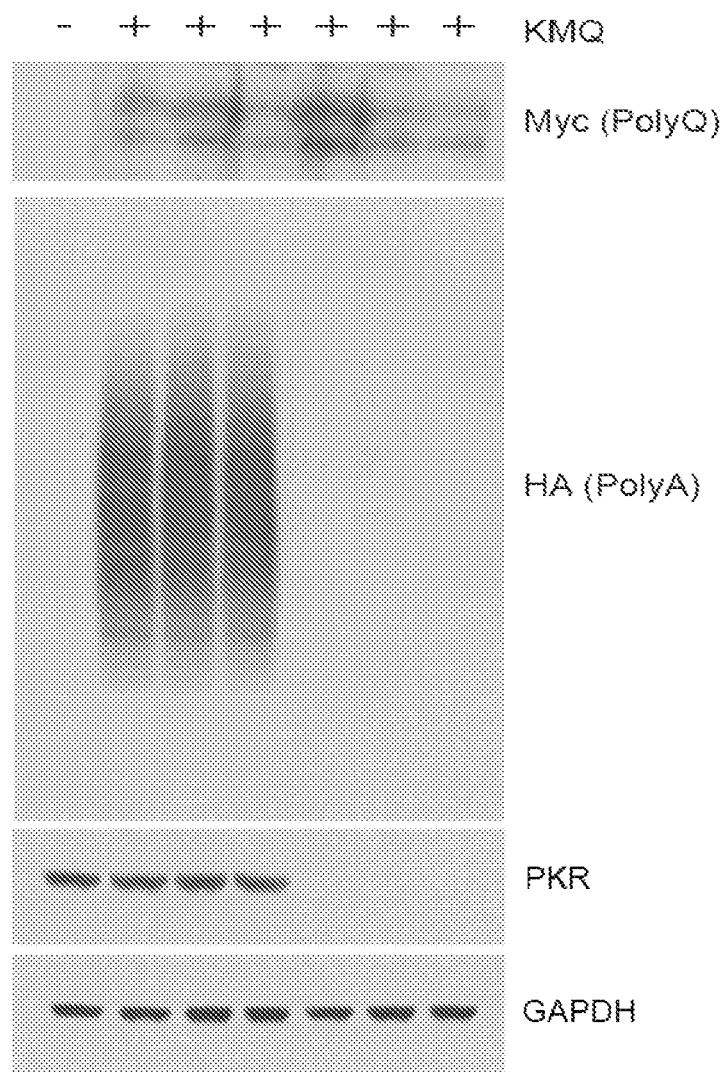

To independently test the role of PKR in RAN translation, a HEK293T PKR knock-out cell line was produced using CRISPR/Cas9. In some embodiments, PKR KO cells show reduced levels of polyAla expressed from CAG expansions (e.g., relevant to DM1, SCA1,2,3,6,7,8,17, DRPLA, HD, HDL2, SBMA, etc.), and CCUG and CAGG repeat expansion RNAs (e.g., relevant to myotonic dystrophy type 2). Transient transfections using CAG, CCTG, CAGG expansion constructs show a dramatic reduction of polyAla, polyLPAC and polyQAGR proteins (FIG. 9).

Taken together, these results, indicate that in some embodiments, PKR activation, including activation by repeat expansion RNAs, increases RAN protein levels through the eIF2-α phosphorylation pathway.

Figure 10A:
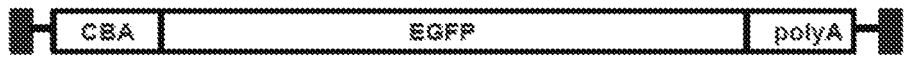
FIGS. 10A-10D show inhibition of PKR pathway decreases RAN protein aggregates and improves behavioral phenotypes in C9-500 BAC transgenic mice.
Figure 10A:
Figure 10B:
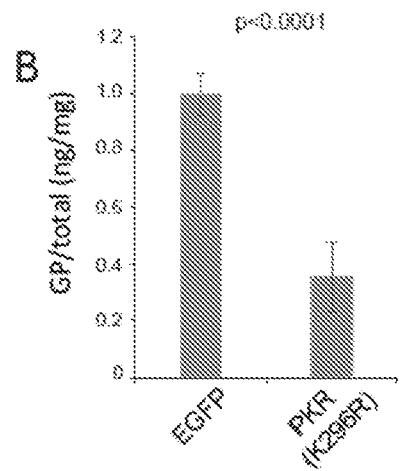
Figure 10C:
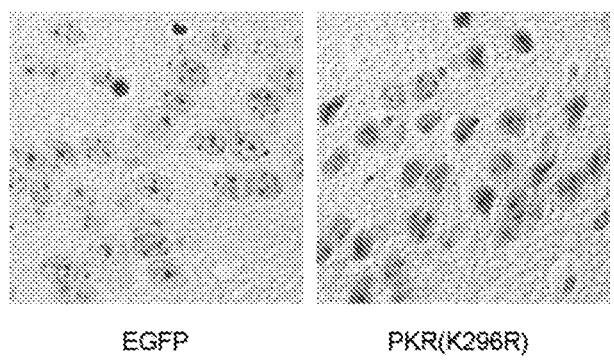
Figure 10C:
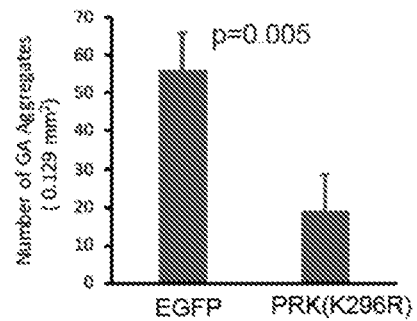
Figure 10D:
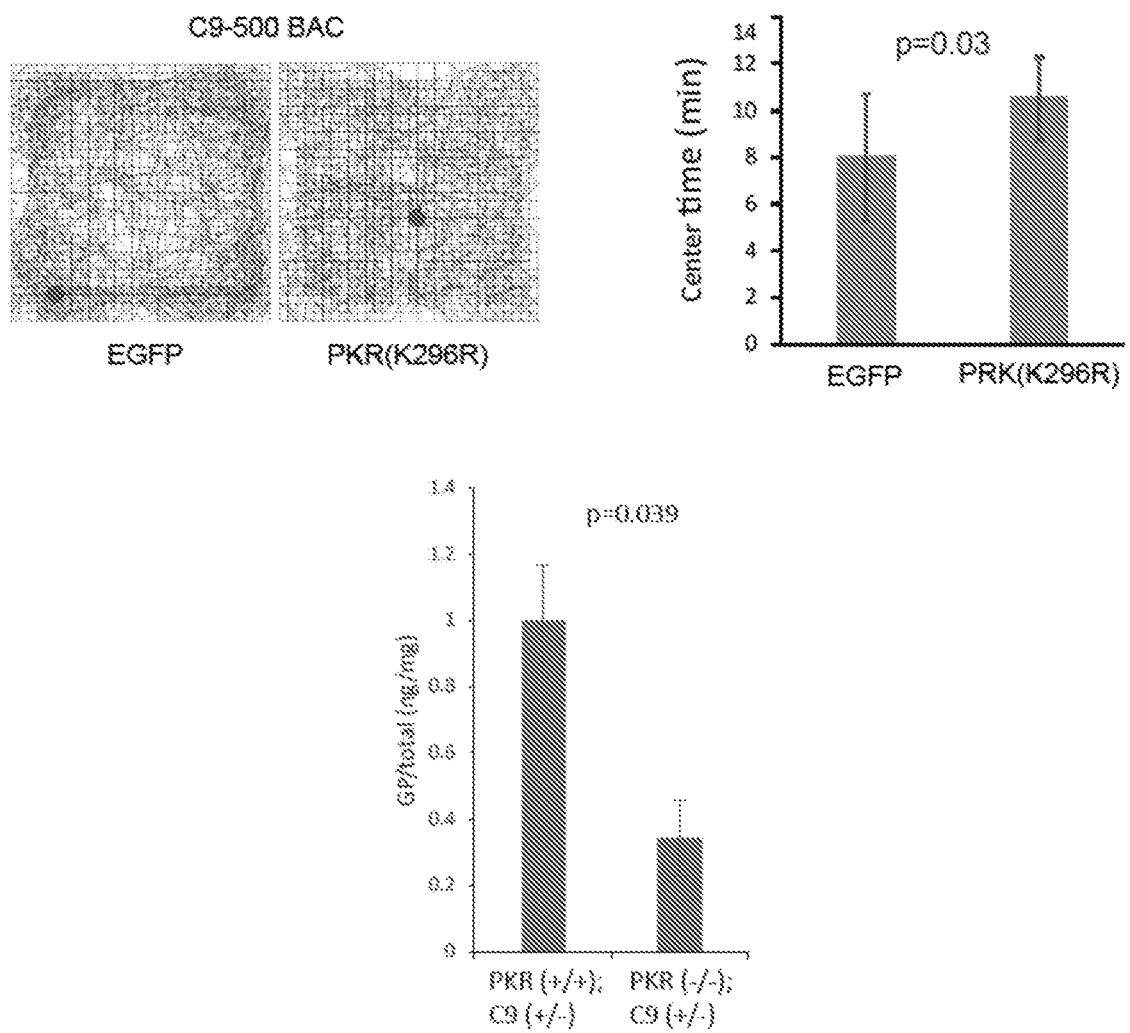

Effects of PKR on RAN Translation in the C9-500 Mouse Model.

rAAV-mediated delivery of dominant negative PKR-K296R, or EGFP as a control, was performed using intracerebroventricular (ICV) injections at P0 in C9orf72 ALS/FTD BAC transgenic mice (C9-BAC) and non-transgenic (NT) littermate controls. A schematic depiction of each construct is described in FIG. 10A. Four groups of animals (EGFP/C9, EGFP/NT, PKR-K296R/C9 and PKR-K296R/NT) were aged to 3 months. Genotyping was done by both PCR and Southern blot analyses, which indicated that C9 treatment and control groups had comparable repeat expansion sizes. Immunohistochemistry (IHC) using a monoclonal GA antibody indicated C9 mice treated with PKR-K296R had decreased numbers of GA aggregates in the retrosplenial cortex compared to C9 EGFP controls (FIGS. 10B-10C). Similarly, soluble GP levels, detected by mesoscale detection (MSD) assays, were reduced in brain lysates from C9 PKR-K296R treated animals compared to C9 EGFP controls. PKR-K296R treated animals showed improvement in open field testing with increased center time compared to C9 EGFP control animals (FIG. 10D). Additionally, DigiGait analyses indicated that of the 15 parameters that differed between untreated C9-500 and NT EGFP injected controls at 12 weeks, nine of these parameters improved in C9 PKR-K296R treated animals. Additionally, animals from the C9 PKR-K296R treatment group showed similar performance by DigiGait with only 2 of 15 parameters significantly different between C9 PKR-K296R and NT treatment groups.

Metformin Decreases RAN Translation and Mitigates Repeat-Induced PKR Activation

Figure 11A:
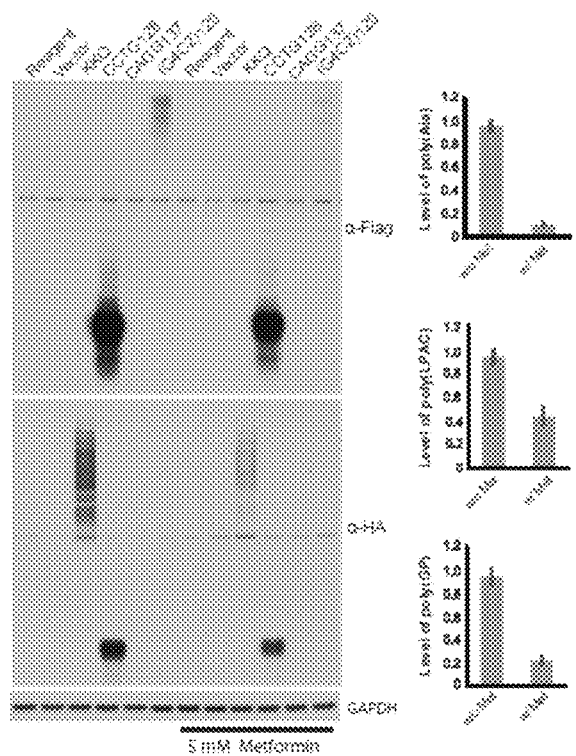
FIGS. 11A-11J show metformin inhibits PKR and reduces RAN proteins and ameliorates disease in C9-BAC mice.
Figure 11B:
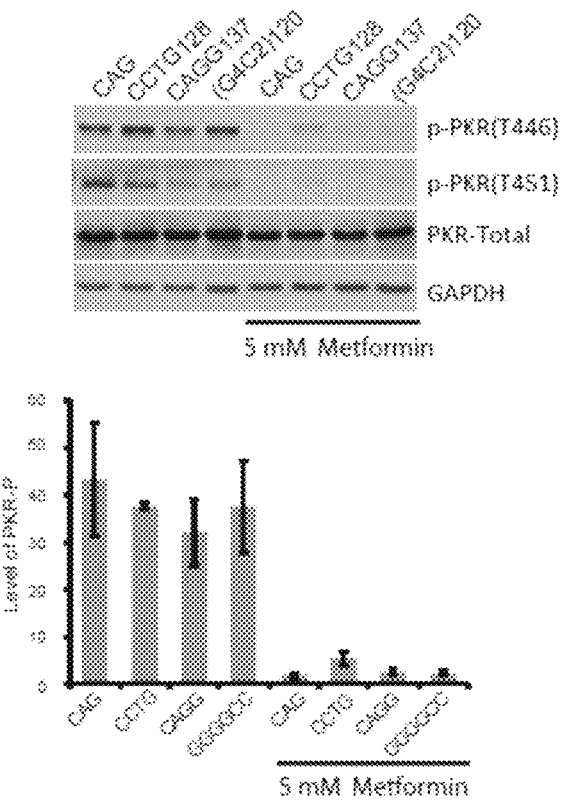
Figure 12:
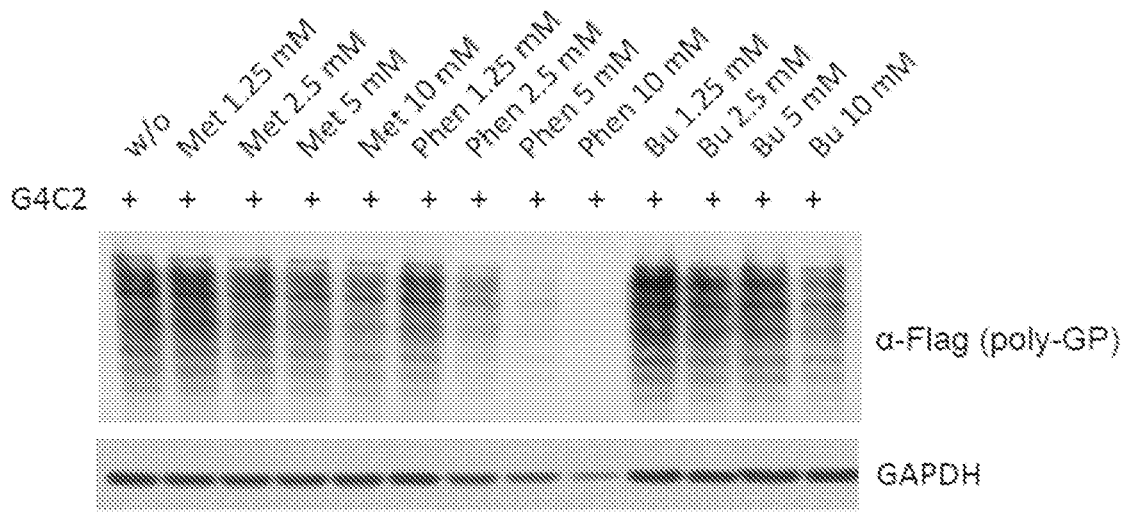
FIG. 12 shows metformin and related drugs phenformin and buformin inhibit PKR and reduce GP RAN protein levels in dose-dependent manner. Top panel: protein blots showing metformin, phenformin and buformin reduce RAN GP protein levels in HEK293T cells transiently transfected with G4C2 expansion constructs in a dose dependent manner. Bottom panel: metformin, phenformin and buformin reduce levels of p-PKR (T446 and T451) in cells transfected with a G4C2 repeat expansion construct.
Figure 12:
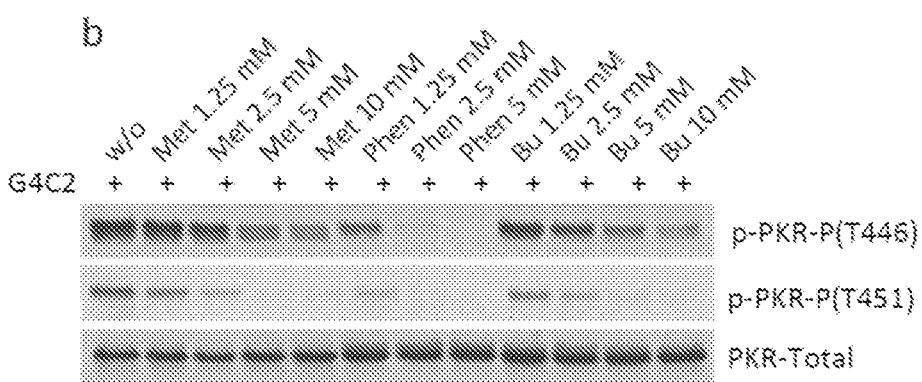

It was observed that, in some embodiments, metformin decreases RAN protein levels in cells expressing CAG, CCUG or G4C2 expansion RNAs (FIG. 11A). RAN protein inhibition by metformin is similar to the inhibition with PKR-K296R, indicating that metformin mitigates PKR activation induced by repeat expansion RNAs. Transient transfections of expansion constructs treated with or without metformin were performed. Protein blots indicate that metformin decreases PKR phosphorylation at T446 and T451, sites which have been observed to be required for PKR activation (FIG. 11B). Additionally, metformin and the related drugs phenformin and buformin mediate similar dose-dependent inhibition of G4C2 repeat-expansion induced p-PKR levels and RAN polyGP levels (FIG. 12).

In summary, metformin reduced the levels of several types of RAN proteins in mammalian cells and PKR was identified as a metformin target that inhibits PKR activation and eIF2α phosphorylation.

Metformin Ameliorates Neuropathological and Behavioral Phenotypes in the C9-500 Mouse Model.

Figure 11C:
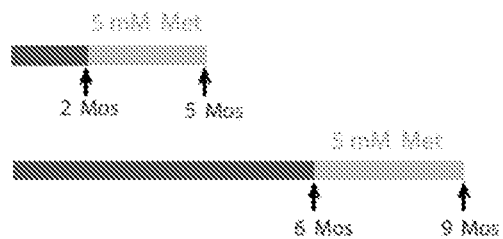
Figure 11D:
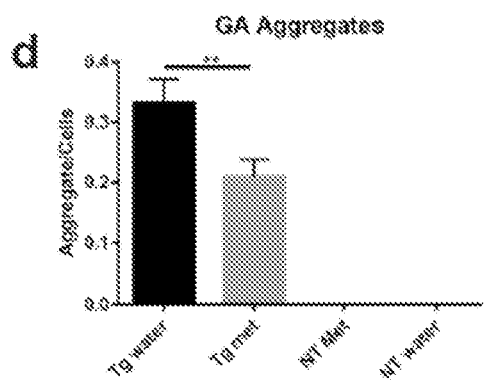
Figure 11E:
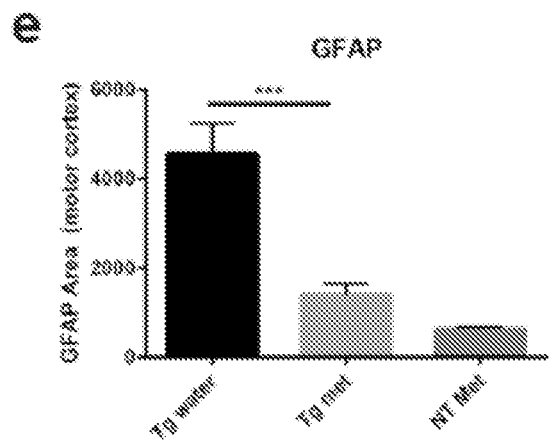
Figure 11F:
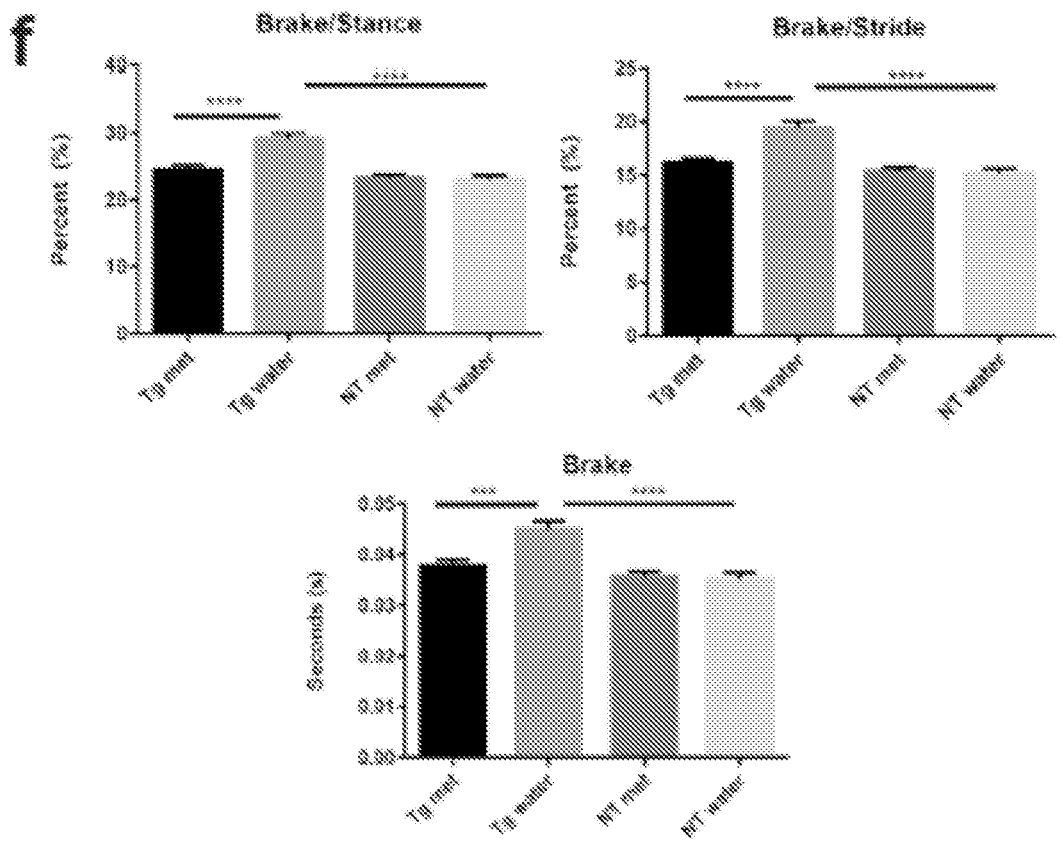
Figure 11G:
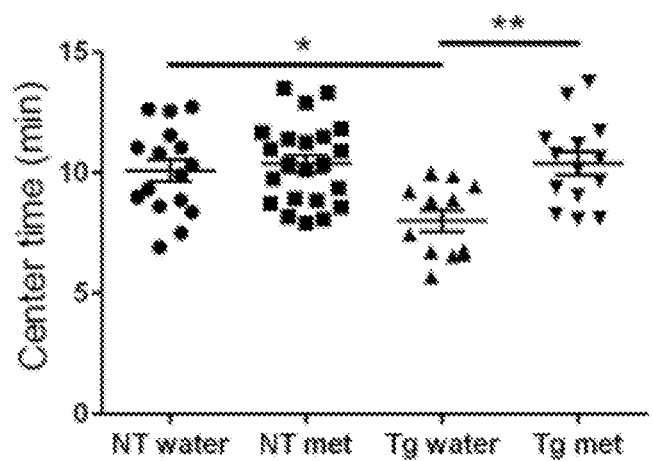

C9orf72 mice, C9-500 BAC and NT mice were treated for 3 months with or without metformin (5 mg/ml) in the drinking water. In Group A animals, treatment began at 2 months of age, before the onset of overt behavioral or pathological phenotypes. In Group B, smaller cohorts of animals (n=8/group) were treated beginning at 6 months, an age at which behavioral phenotypes are evident. A schematic depicting treatment regimens is shown in FIG. 11C. Digi-Gait analyses of Group A mice at 5 months identified eight DigiGait parameters that differed between untreated C9 and NT cohorts. In C9 metformin treated mice, six of these parameters improved compared to the C9 water treatment group (FIGS. 11E-11G). Similarly, Group A metformin-treated C9 mice showed increased center time by open field testing, compared to untreated C9 mice. These data indicate that this anxiety-like behavior is improved by metformin treatment (FIG. 11G).

Figure 11H:
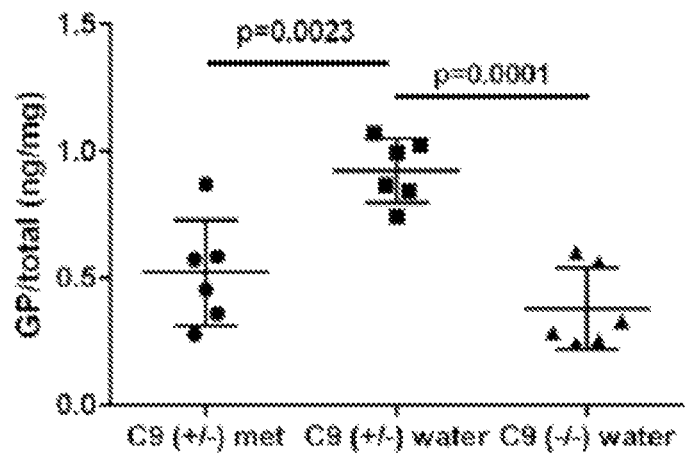
Figure 11I:
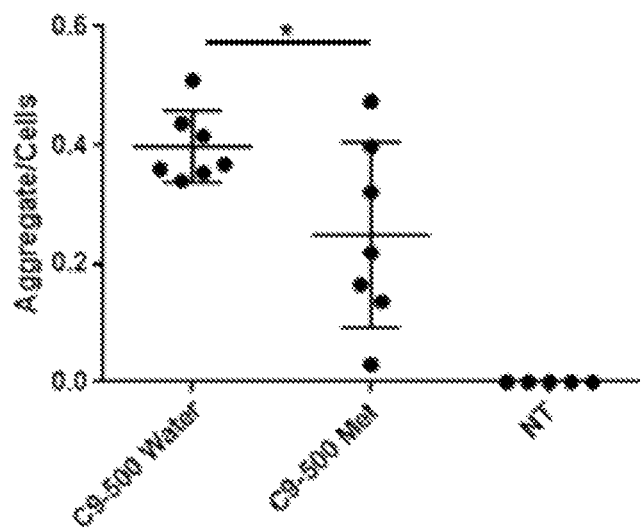

IHC staining of Group A animals for glial fibrillary acidic protein (GFAP), a marker of neuroinflammation previously reported in our C9-BAC mice, was significantly reduced in C9 metformin treated compared to untreated C9 animals (FIG. 11E). Additionally, C9 metformin treated animals showed decreased numbers of GA aggregates in the retrosplenial cortex compared to C9 controls in cohorts that began treatment at presymptomatic (8 wks, Group A) or symptomatic ages (6 mos, Group B) (FIG. 11D). Decreases in soluble GP levels were observed in C9 metformin treated animals compared to C9 controls in the older Group B but not the younger Group A treatment cohorts (FIGS. 11H-11I).

Figure 11J:
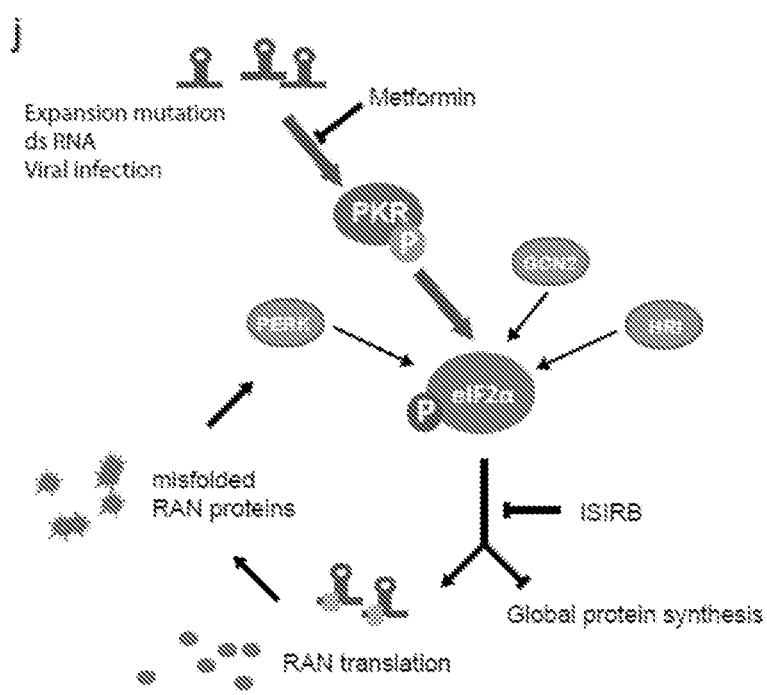

Taken together, data indicate that metformin reduces RAN protein levels in vitro and in vivo, and metformin treatment improves behavior and decreases neuroinflammation in C9 BAC transgenic mice. In some embodiments, data described in this example are consistent with a model in which repeat expansion RNAs lead to chronic activation of the PKR pathway, a condition which results in increased levels of p-eIF2α, decreases in global protein synthesis and the upregulation of RAN translation (FIG. 11J).

Example 3

Figure 13A:
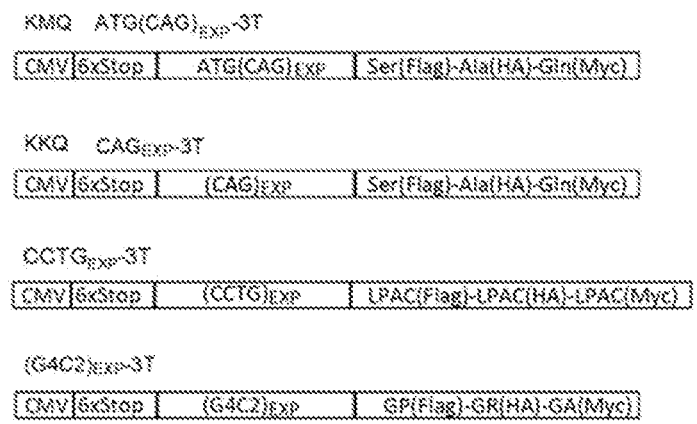
FIGS. 13A-13B show metformin inhibits RAN translation in multiple reading frames in cells that have been transfected with constructs containing CAG, CCTG or GGGGCC repeat expansion motifs. Protein blots were run on protein lysates from HEK293T cells transfected with various repeat expansion constructs shown in FIG. 13A.
Figure 13B:
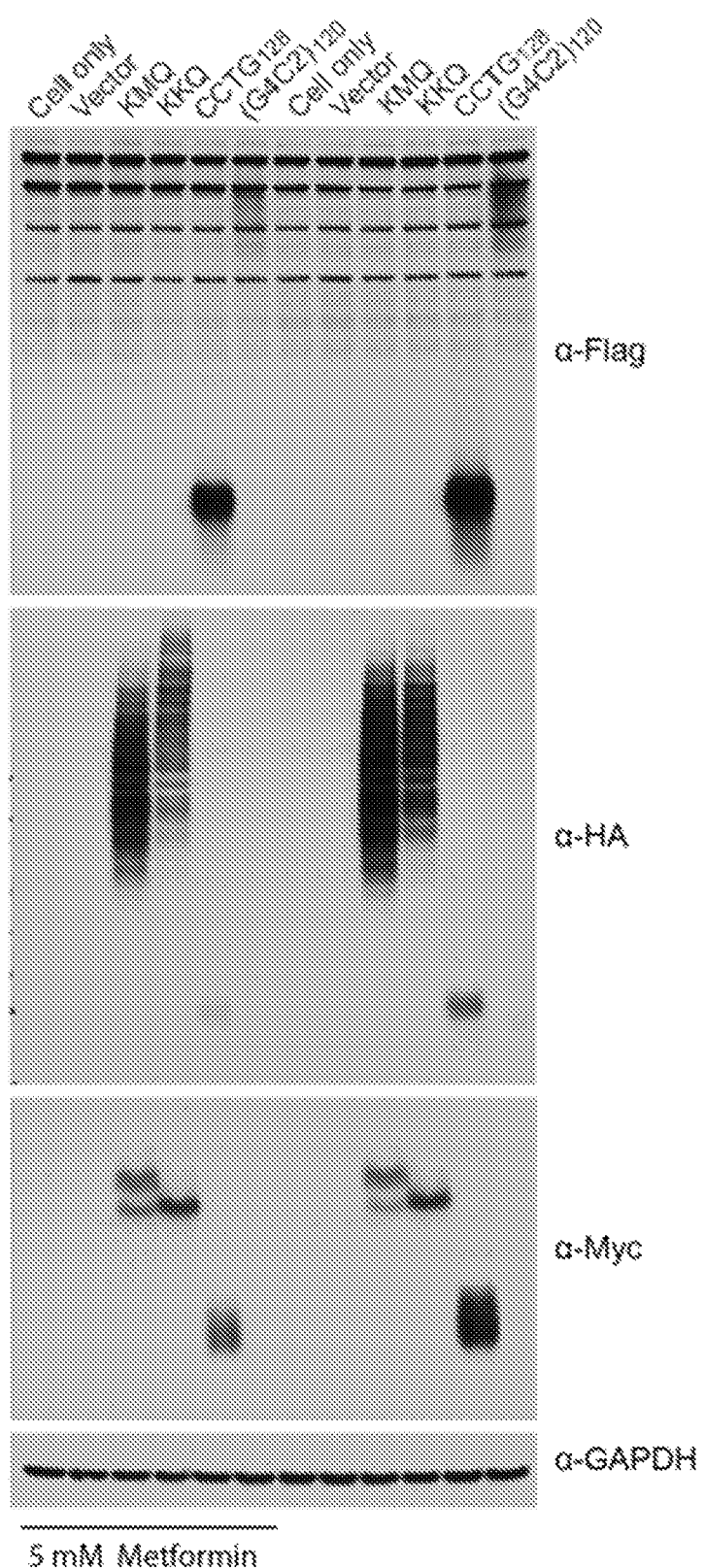

Metformin was evaluated for its effect on RAN protein translation in HEK293T cells that have been transfected with constructs containing CAG, CCTG or GGGGCC repeat expansion motifs. Transfected HEK293T cells were treated with metformin. Protein blots were run on protein lysates from HEK293T cells transfected with various repeat expansion constructs shown in FIG. 13A. In FIG. 13B, the lanes labeled KMQ, show: RAN poly-Ser-Flag, RAN poly-Ala-HA, ATG initiated polyGln-Myc. In FIG. 13B the lanes labeled KMQ has a methionine encoding ATG immediately 5' to the CAG repeat expansion and located within the polyGln reading frame. The lanes labeled KKQ indicate the KKQ vector contains a CAG expansion without an AUG initiation codon, and indicates: RAN polySer-Flag, RAN polyAla-HA, RAN polyGln-Myc. These constructs contain epitope tags that are incorporated into the C-terminal regions of the ATG-initiated poly-Gln and non-ATG initiated RAN proteins (poly-Gln, poly-Leu-Pro-Ala-Cys and poly-Gly-Pro) which are expressed across these repeat expansions. The lane labeled CCTG expresses the following RAN proteins: RAN polyLPAC-Flag, RAN polyLPAC-HA, RAN polyLPAC-Myc. The lane labeled G4C2 is designed to detect the following RAN proteins: RAN polyGP-Flag, RAN polyGR-HA, RAN polyGA-Myc. The protein blots in FIG. 13B show reduced RAN protein levels of the following RAN proteins of poly-LPAC (poly-Leucine-Proline-Alanine-Cysteine) in all three reading frames, poly-Ala, and poly-GP (poly glycine-proline). FIG. 13B shows that metformin inhibits RAN protein accumulation in cells transfected with exemplary repeat expansion constructs.

Figure 14:
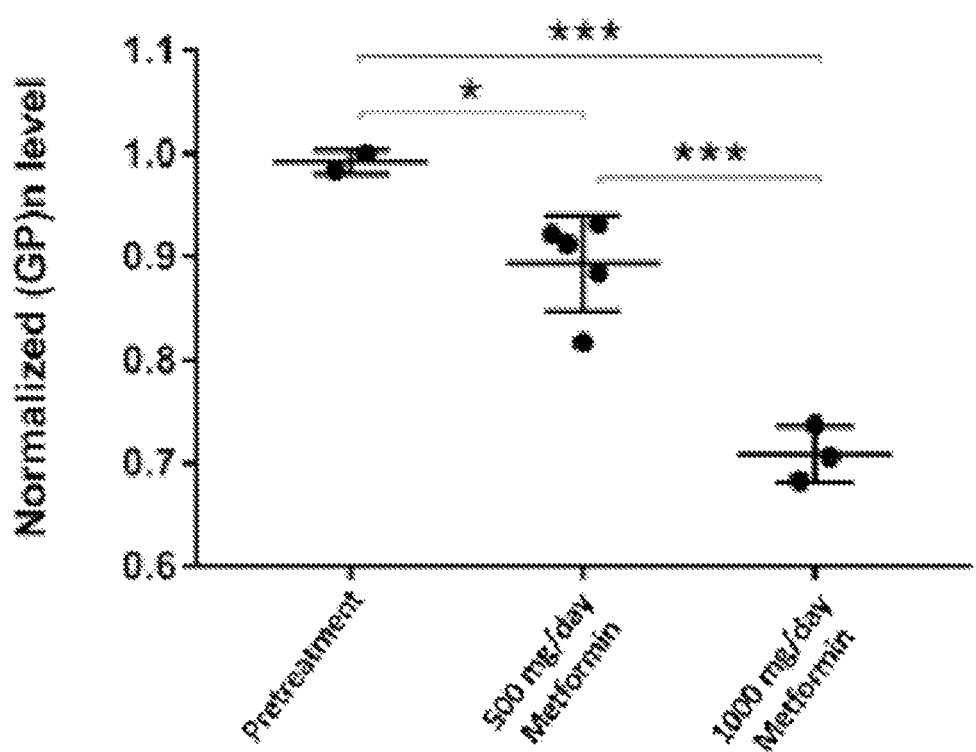
FIG. 14 shows normalized $(GP)_n$ level for the following conditions: Pretreatment, 500 mg/day Metformin, and 1000 mg/day Metformin.

Metformin was evaluated for its effect on the steady state levels of glycine-proline (GP) RAN protein detected in vivo in proteins extracted from peripheral blood of a C9ORF72 expansion-positive study subject before and after treatment with metformin C9ORF72. These levels were measured in a human study subject before and after the subject was administered metformin (500 mg or 1000 mg per day Metformin Hydrochloride Extended Release Tablets) at different doses as prescribed by the subject's physician. Dose dependent reduction of glycine-proline (GP) RAN protein levels was observed in blood samples taken from a single human subject with a C9ORF72 repeat expansion compared to pretreatment levels. GP levels were measured in protein lysates from leukocytes isolated from peripheral blood and at multiple time points between 10 and 30 days after treatment with 500 or 1000 mg/day of metformin. $*p<0.05$, $***p<0.001$, after correction for multiple comparisons. FIG. 14 shows that metformin reduces the levels of RAN proteins generated by expression of C9ORF72 in vivo.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding,"

"composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A method of inhibiting repeat non-ATG protein (RAN protein) translation, the method comprising contacting a cell expressing a RAN protein with an effective amount of a protein kinase R (PKR) inhibitor.

2. The method of claim 1, wherein the RAN protein is a poly-Alanine, poly-Leucine, poly-Serine, poly-Cysteine, poly-Glutamine, poly-Leu-Pro-Ala-Cys, poly-Gln-Ala-Gly-Arg, poly-Gly-Pro, poly-Gly-Arg, poly-Gly-Ala, or poly-Pro-Ala, poly-Pro-Arg, poly-Gly-Pro.

3. The method of claim 1, wherein the RAN protein is encoded by a gene associated with Huntington's disease (HD, HDL2), Fragile X Syndrome (FRAXA), Spinal Bulbar Muscular Atrophy (SBMA), Dentatorubropallidoluysian Atrophy (DRPLA), Spinocerebellar Ataxia 1 (SCA1), Spinocerebellar Ataxia 2 (SCA2), Spinocerebellar Ataxia 3 (SCA3), Spinocerebellar Ataxia 6 (SCA6), Spinocerebellar Ataxia 7 (SCAT), Spinocerebellar Ataxia 8 (SCA8), Spinocerebellar Ataxia 12 (SCA12), or Spinocerebellar Ataxia 17 (SCA17), amyotrophic lateral sclerosis (ALS), Spinocerebellar ataxia type 36 (SCA36), Spinocerebellar ataxia type 29 (SCA29), Spinocerebellar ataxia type 10 (SCA10), myotonic dystrophy type 1 (DM1), myotonic dystrophy type 2 (DM2), or Fuch's Corneal Dystrophy.

4. The method of claim 1, wherein the PKR inhibitor inhibits PKR expression or activity.

5. The method of claim 1, wherein the PKR inhibitor is a protein, a nucleic acid, or a small molecule.

6. The method of claim 1, wherein the PKR inhibitor is a selective PKR inhibitor.

7. The method of claim 1, wherein the PKR inhibitor is an inhibitory nucleic acid, optionally wherein the inhibitory nucleic acid is a dsRNA, siRNA, shRNA, mi-RNA, artificial miRNA (ami-RNA), antisense oligonucleotide (ASO) or RNA aptamer.

8. The method of claim 1, wherein the PKR inhibitor is a dominant negative variant of PKR.

9. The method of claim 1, wherein the PKR inhibitor is delivered to the cell by a viral vector, optionally wherein the viral vector is a recombinant adeno-associated virus (rAAV).

10. The method of claim 9, wherein the rAAV comprises an AAV9 capsid protein or variant thereof.

11. The method of claim 8, wherein the dominant negative variant of PKR comprises a K296R mutation.

\* \* \* \* \*

UNITED STATES PATENT AND TRADEMARK OFFICE
CERTIFICATE OF CORRECTION

PATENT NO. : 11,345,911 B2
APPLICATION NO. : 16/605992
DATED : May 31, 2022
INVENTOR(S) : Laura Ranum et al.

It is certified that error appears in the above-identified patent and that said Letters Patent is hereby corrected as shown below:

In the Claims

In Claim 3, Column 45, Line 16, the text "Ataxia 7 (SCAT)" should read -- Ataxia 7 (SCA7) --

Signed and Sealed this
Ninth Day of August, 2022

Katherine Kelly Vidal
*Director of the United States Patent and Trademark Office*

```
                              SEQUENCE LISTING

<160> NUMBER OF SEQ ID NOS: 14

<210> SEQ ID NO 1
    <211> LENGTH: 330
    <212> TYPE: DNA
    <213> ORGANISM: Artificial Sequence
    <220> FEATURE:
    <223> OTHER INFORMATION: Synthetic polynucleotide

<400> SEQUENCE: 1
taaaaaatgc agcagcagca gcagcagcag cagcagcagc agcagcagca gcagcagcag        60
cagcagcagc agcagcagca gcagcagcag cagcagcagc agcagcagca gcagcagcag       120
cagcagcagc agcagcagca gcagcagcag cagcagcagc agcagcagca gcagcagcag       180
cagcagcagc agcagcagca gcagcagcag cagcagcagc agcagcagca gcagcagcag       240
cagcagcagc agcagcagca gcagcagcag cagcagcagc agcagcagca gcagcagcag       300
cagcagcagc agcagcagca gcagcagcag                                        330

<210> SEQ ID NO 2
    <211> LENGTH: 330
    <212> TYPE: DNA
    <213> ORGANISM: Artificial Sequence
    <220> FEATURE:
    <223> OTHER INFORMATION: Synthetic polynucleotide

<400> SEQUENCE: 2
taaaaaaagc agcagcagca gcagcagcag cagcagcagc agcagcagca gcagcagcag        60
cagcagcagc agcagcagca gcagcagcag cagcagcagc agcagcagca gcagcagcag       120
cagcagcagc agcagcagca gcagcagcag cagcagcagc agcagcagca gcagcagcag       180
cagcagcagc agcagcagca gcagcagcag cagcagcagc agcagcagca gcagcagcag       240
cagcagcagc agcagcagca gcagcagcag cagcagcagc agcagcagca gcagcagcag       300
cagcagcagc agcagcagca gcagcagcag                                        330

<210> SEQ ID NO 3
    <211> LENGTH: 20
    <212> TYPE: PRT
    <213> ORGANISM: Artificial Sequence
    <220> FEATURE:
    <223> OTHER INFORMATION: Synthetic polypeptide

<400> SEQUENCE: 3

Ala Ala Ala Ala Ala Ala Ala Ala Ala Ala Ala Ala Ala Ala Ala Ala
    1               5                   10                  15

Ala Ala Ala Ala
                20

<210> SEQ ID NO 4
    <211> LENGTH: 18
    <212> TYPE: PRT
    <213> ORGANISM: Artificial Sequence
    <220> FEATURE:
```

-continued

```
<223> OTHER INFORMATION: Synthetic polypeptide

<400> SEQUENCE: 4

Leu Leu Leu Leu Leu Leu Leu Leu Leu Leu Leu Leu Leu Leu Leu Leu
1               5                   10                  15

Leu Leu

<210> SEQ ID NO 5
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 5

Ser Ser Ser Ser Ser Ser Ser Ser Ser Ser Ser Ser Ser Ser Ser Ser
1               5                   10                  15

Ser Ser Ser Ser
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 6

Cys Cys Cys Cys Cys Cys Cys Cys Cys Cys Cys Cys Cys Cys Cys Cys
1               5                   10                  15

Cys Cys Cys Cys
            20

<210> SEQ ID NO 7
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 7

Gly Pro Gly Pro Gly Pro Gly Pro Gly Pro Gly Pro Gly Pro Gly Pro
1               5                   10                  15

Gly Pro Gly Pro
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 8

Gly Ala Gly Ala Gly Ala Gly Ala Gly Ala Gly Ala Gly Ala Gly Ala
1               5                   10                  15

Gly Ala Gly Ala
            20

<210> SEQ ID NO 9
<211> LENGTH: 20
<212> TYPE: PRT
<213> ORGANISM: Artificial Sequence
<220> FEATURE:
```

<223> OTHER INFORMATION: Synthetic polypeptide

<400> SEQUENCE: 9

Gly Arg Gly Arg Gly Arg Gly Arg Gly Arg Gly Arg Gly Arg Gly Arg
1               5                   10                  15

Gly Arg Gly Arg
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 10

Pro Ala Pro Ala Pro Ala Pro Ala Pro Ala Pro Ala Pro Ala Pro Ala
1               5                   10                  15

Pro Ala Pro Ala
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 11

Pro Arg Pro Arg Pro Arg Pro Arg Pro Arg Pro Arg Pro Arg Pro Arg
1               5                   10                  15

Pro Arg Pro Arg
            20

<210> SEQ ID NO 12
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 12

Leu Pro Ala Cys Leu Pro Ala Cys Leu Pro Ala Cys
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 13

Gln Ala Gly Arg Gln Ala Gly Arg Gln Ala Gly Arg
1               5                   10

<210> SEQ ID NO 14
<211> LENGTH: 145
<212> TYPE: DNA
<213> ORGANISM: Artificial Sequence
<220> FEATURE:
<223> OTHER INFORMATION: Synthetic polynucleotide

<400> SEQUENCE: 14
ttggccactc cctctctgcg cgctcgctcg ctcactgagg ccgggcgacc aaaggtcgcc      60

```
cgacgcccgg gctttgcccg ggcggcctca gtgagcgagc gagcgcgcag agagggagtg      120
gccaactcca tcactagggg ttcct                                            145
```